US012805960B2

(12) United States Patent
Brett

(10) Patent No.: US 12,805,960 B2
(45) **Date of Patent: *Nov. 24, 2026**

(54) GLOVE DONNING APPARATUS AND METHOD

(71) Applicant: Kenton Brett, Indianapolis, IN (US)

(72) Inventor: Kenton Brett, Indianapolis, IN (US)

(73) Assignee: Kenton Brett, Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/800,701

(22) Filed: Aug. 12, 2024

(65) Prior Publication Data

US 2025/0041014 A1 Feb. 6, 2025

Related U.S. Application Data

(63) Continuation of application No. 17/499,766, filed on Oct. 12, 2021, now Pat. No. 12,064,205.

(60) Provisional application No. 63/134,155, filed on Jan. 5, 2021, provisional application No. 63/090,223, filed on Oct. 10, 2020.

(51) Int. Cl.
*A61B 42/50* (2016.01)

(52) U.S. Cl.
CPC .................................... *A61B 42/50* (2016.02)

(58) Field of Classification Search
CPC ........ A47G 25/904; A61B 42/40; A61B 42/50
See application file for complete search history.

(56) References Cited

U.S. PATENT DOCUMENTS

| | | | | |
|---|---|---|---|---|
| 1,507,875 | A | 9/1924 | Weis et al. | |
| 1,938,685 | A | 12/1933 | Breuls et al. | |
| 1,996,377 | A | 4/1935 | Hinchen | |
| 2,641,767 | A | 6/1953 | La | |
| 2,933,102 | A | 4/1960 | Hillman et al. | |
| 3,067,001 | A | 12/1962 | Mccollum | |
| 3,695,493 | A * | 10/1972 | Karr | A47G 25/904 223/111 |
| 4,002,276 | A | 1/1977 | Poncy et al. | |
| 4,099,270 | A | 7/1978 | Jabour | |
| 4,275,812 | A | 6/1981 | Poncy et al. | |
| 4,889,266 | A * | 12/1989 | Wight | A61B 42/40 223/111 |
| 4,909,413 | A | 3/1990 | McCutcheon | |
| 4,915,272 | A | 4/1990 | Vlock | |
| 5,058,785 | A | 10/1991 | Rich et al. | |
| 5,078,308 | A | 1/1992 | Sullivan | |
| 5,725,763 | A | 3/1998 | Bonhomme | |
| 5,868,290 | A | 2/1999 | Green et al. | |
| 5,878,909 | A | 3/1999 | Rogow | |
| 6,021,935 | A | 2/2000 | Yonezawa | |
| 6,053,380 | A | 4/2000 | Sherrod | |

(Continued)

OTHER PUBLICATIONS

Firstaidtoday, director. YouTube, YouTube, Apr. 11, 2010, https://www.youtube.com/watch?v=emv1ELKR8FY. Accessed Feb. 7, 2022.

(Continued)

*Primary Examiner* — F Griffin Hall
(74) *Attorney, Agent, or Firm* — Maginot, Moore & Beck, LLP

(57) ABSTRACT

A glove donning system is disclosed herein. The glove donning system presents a pair of inflated gloves for a user to easily don, then resets to present another pair.

16 Claims, 34 Drawing Sheets

(56) References Cited

U.S. PATENT DOCUMENTS

| | | | |
|---|---|---|---|
| 6,343,425 B1 | 2/2002 | Sias et al. | |
| 6,375,034 B1 | 4/2002 | Corbett | |
| 6,516,469 B1 | 2/2003 | Schaetzel | |
| 6,557,462 B1 | 5/2003 | Wang | |
| 6,752,287 B1 | 6/2004 | Lin | |
| 6,932,253 B2 | 8/2005 | Sato | |
| 6,953,130 B2 | 10/2005 | Corbett | |
| 7,377,410 B1 | 5/2008 | Webb | |
| 7,434,594 B1 | 10/2008 | Robbins et al. | |
| 7,480,945 B2 | 1/2009 | Knuth et al. | |
| 8,146,776 B2 | 4/2012 | Balkin et al. | |
| 8,657,151 B2 | 2/2014 | Balkin et al. | |
| 8,807,402 B2 | 8/2014 | Backhaus et al. | |
| 8,855,810 B2 | 10/2014 | Chuah | |
| 9,295,352 B2 | 3/2016 | Williams | |
| 9,414,706 B2 | 8/2016 | Purcell et al. | |
| 9,573,740 B2 | 2/2017 | Cannon | |
| 9,925,015 B2 | 3/2018 | Gravlee | |
| 9,949,587 B2 | 4/2018 | Hansen | |
| 9,957,125 B2 | 5/2018 | Ray | |
| 10,098,699 B1 | 10/2018 | Buck | |
| 10,123,644 B2 | 11/2018 | Purcell et al. | |
| 10,143,528 B2 | 12/2018 | Gaines et al. | |
| 10,219,643 B2 | 3/2019 | Purcell et al. | |
| 10,314,422 B2 | 6/2019 | Purcell et al. | |
| 10,349,769 B2 | 7/2019 | Avshalom et al. | |
| 10,512,516 B1 | 12/2019 | Rogers et al. | |
| 10,786,021 B2 | 9/2020 | Harrison et al. | |
| 10,799,310 B2 | 10/2020 | Gaines et al. | |
| 10,849,703 B2 | 12/2020 | Backhaus et al. | |
| 10,912,405 B1 | 2/2021 | McCarthy | |
| 11,324,562 B2 | 5/2022 | Moghadam | |
| 11,388,940 B2 * | 7/2022 | Narahari | A41D 19/046 |
| 2002/0043810 A1 | 4/2002 | Dooley | |
| 2005/0229287 A1 | 10/2005 | Mattesky | |
| 2005/0257839 A1 | 11/2005 | Kaneko et al. | |
| 2007/0062970 A1 | 3/2007 | Agahi et al. | |
| 2008/0073388 A1 | 3/2008 | Saegusa et al. | |
| 2022/0395345 A1 | 12/2022 | Shalom Avshalom | |

OTHER PUBLICATIONS

Weldbuiltkb, director. YouTube, YouTube, Apr. 7, 2016, https://www.youtube.com/watch?v=pzCnovFCIAs&t=4s. Accessed Feb. 7, 2022.

Sani Hands, YouTube, YouTube, Nov. 9, 2013, https://www.youtube.com/watch?v=FDKLNgRNxbg. Accessed Feb. 7, 2022.

Glove Assist—2016 Promotional Video, YouTube, YouTube, Apr. 13, 2016, https://www.youtube.com/watch?v=PmTFnS0bgDU. Accessed Feb. 7, 2022.

Revolutionary Invention That Helps to Put on Gloves in Seconds, YouTube, YouTube, Sep. 13, 2019, https://www.youtube.com/watch?v=mUkTe2cZKXs. Accessed Feb. 7, 2022.

Englover—Technical Video (Crimson Startup Summer 2017), YouTube, YouTube, Jul. 26, 2017, https://www.youtube.com/watch?v=7VfFxHOVRSs. Accessed Feb. 7, 2022.

Vitera Touchless Surgical Glove Donning Animation, YouTube, YouTube, Oct. 15, 2013, https://www.youtube.com/watch?v=ES7weoEEvdc. Accessed Feb. 7, 2022.

Autoglove—Mounting Gloves, YouTube, YouTube, Mar. 15, 2019, https://www.youtube.com/watch?v=hifHVxw1VfQ. Accessed Feb. 7, 2022.

GloVac—The Intelligent Glove System, YouTube, YouTube, May 5, 2017, https://www.youtube.com/watch?v=MPaXPn5SaXw. Accessed Feb. 7, 2022.

Automatic Sterile Glove Donning Device, YouTube, YouTube, Jun. 29, 2021, https://www.youtube.com/watch?v=PG55yfzEu9U&t=7s. Accessed Feb. 7, 2022.

"Aeroglove Dispenser—the Only True Non-Touch Gloves in the World." Aeroglove, Dec. 9, 2021, https://www.aeroglove.com/.

* cited by examiner

GLOVE DONNING APPARATUS AND METHOD

CROSS-REFERENCE TO RELATED APPLICATIONS

This application is a continuation of U.S. patent application Ser. No. 17/499,766, filed Oct. 12, 2021, now U.S. Pat. No. 12,064,205, which claims priority to U.S. provisional patent application No. 63/090,223, filed Oct. 10, 2020, and also claims priority to U.S. provisional patent application No. 63/134,155, filed Jan. 5, 2021, the entire contents of which are incorporated herein by reference.

SUMMARY

The present disclosure relates to a glove donning apparatus and method, comprising slides held in a conveyor, each slide packed with a glove, where the conveyor presents a slide to the front opening of the vacuum chamber, where the glove is released into said chamber to be opened via vacuum for the user to don surgical or sterile gloves, exam gloves or non-sterile gloves and other gloves.

BRIEF DESCRIPTION OF THE DRAWINGS

FIG. 7 and.

DETAILED DESCRIPTION

Instructions for donning surgical gloves with sterile technique often break the procedure into 5-20 steps or more. From preparing the sterile field, to cleaning up afterwards, the process can take from 1 to several minutes overall and is not terribly difficult. Still, it could be much quicker and easier. The glove donning apparatus described herein does it in about 3-5 seconds.

Figure 1:
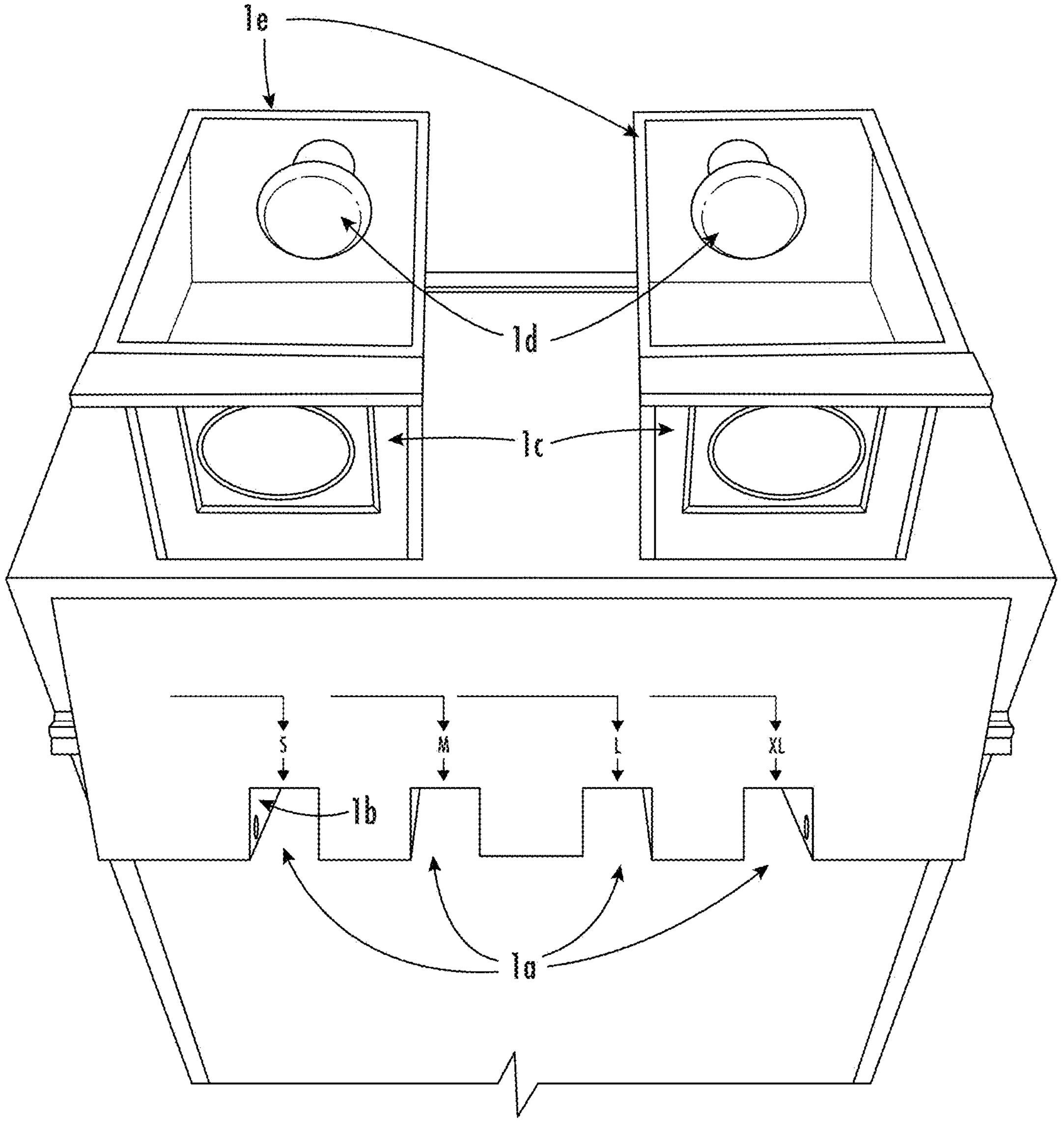
FIG. 1 is a view of an embodiment of the glove donning apparatus of the present disclosure.
Figure 2:
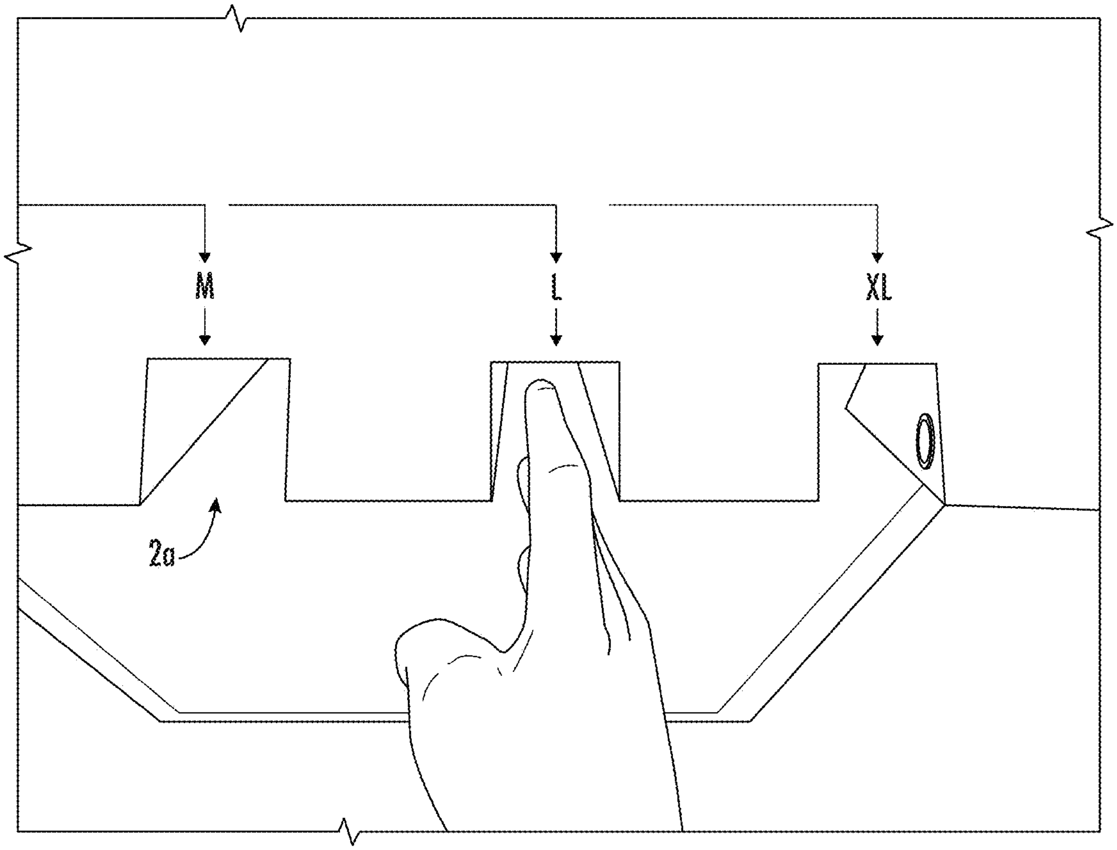
FIG. 2 is a view of the hand swipe slot of the glove donning apparatus shown in FIG. 1.
Figure 3:
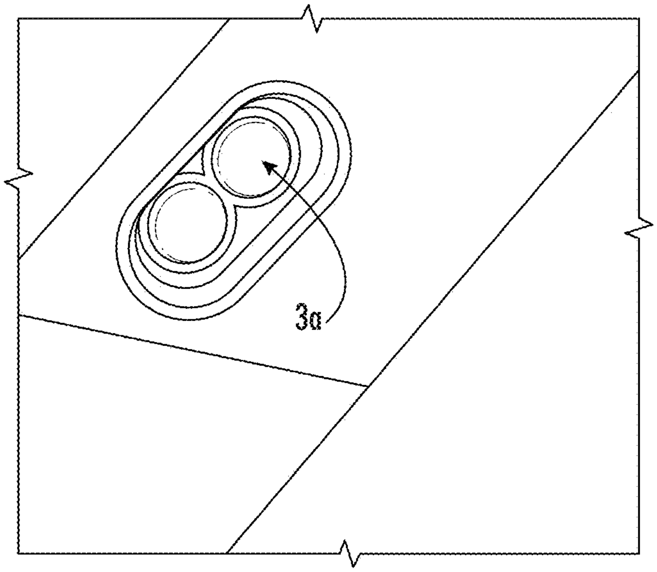
FIG. 3 is a view of an electric eye of the glove donning apparatus shown in FIG. 1.
Figure 4:
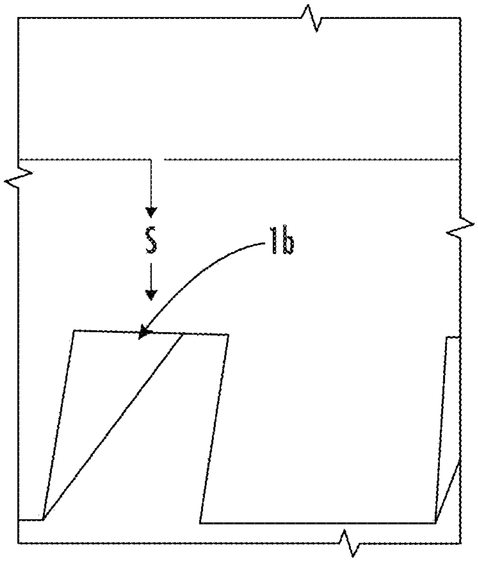
FIG. 4 is a view of a backlit wall of the hand swipe slot shown in FIG. 2.
Figure 5:
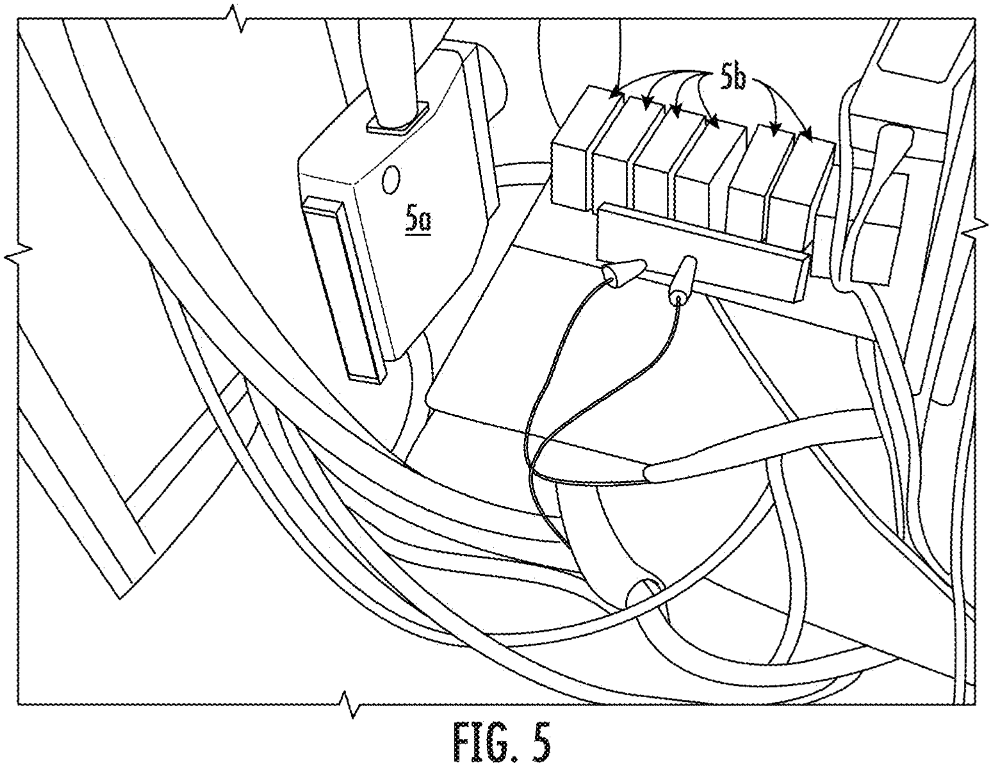
FIG. 5 and FIG. 6 are views of the control system of the glove donning apparatus shown in FIG. 1.
Figure 6:
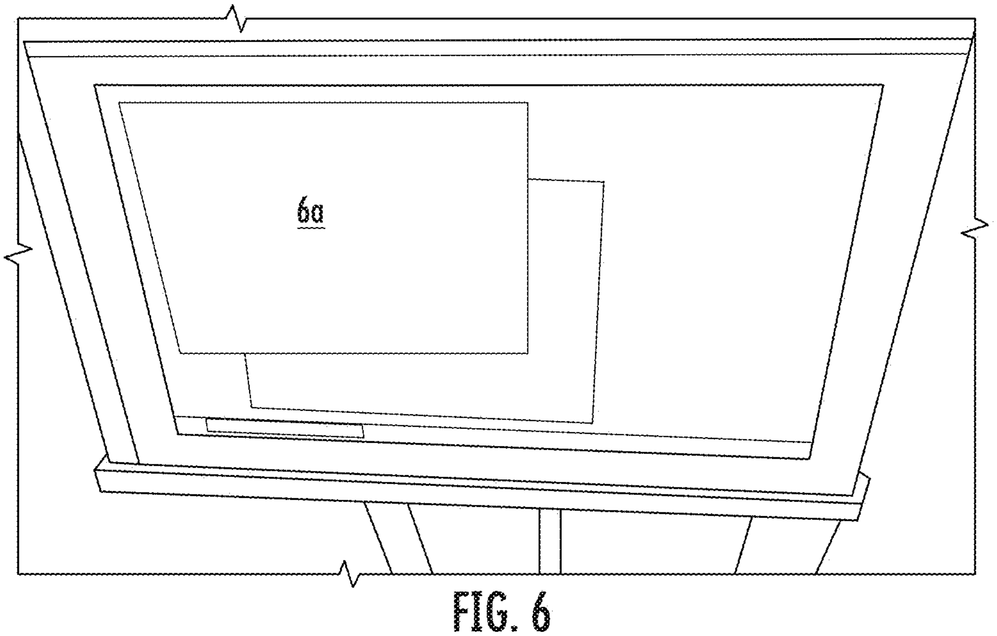

FIG. 1 shows one embodiment of a glove donning apparatus. The control panel has slots 1A, wide enough that users can easily pass their hands (FIG. 2) through the slots 2A without touching anything. Near the front of each slot is an electric eye 3A, of FIG. 3 which may be infrared, which sends a signal to the control system (FIGS. 5 and 6) when a user's hand is passed through the slot. Prototyping using I/O modules 5A and relays 5B of FIG. 5 and display interface 6A of FIG. 6 is straightforward, as are PCB controls for production models using standard engineering practice. 1B of FIG. 4 indicates the slot walls, which can be backlit in green, yellow, red or other colors.

Figure 7:
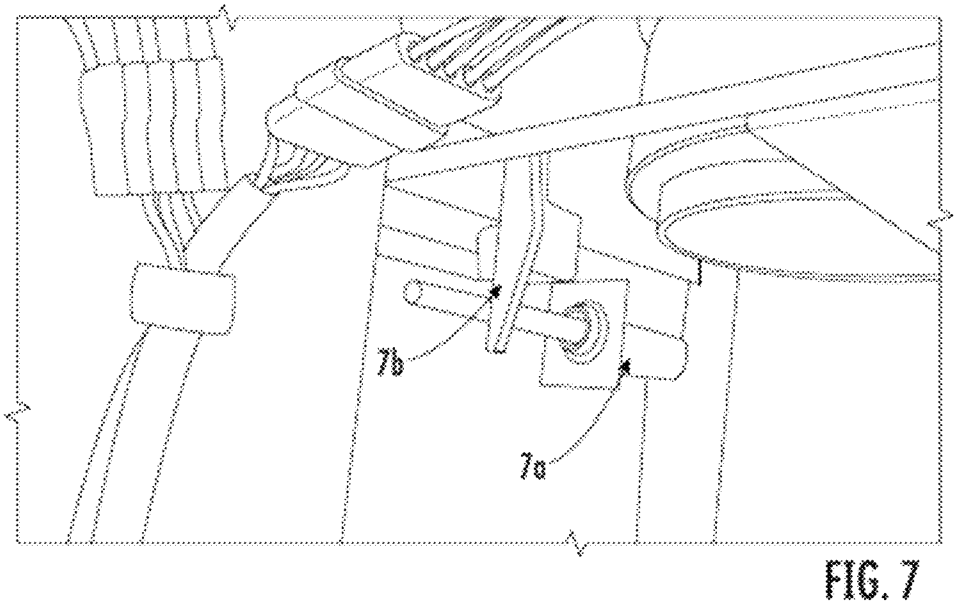
Figure 8:
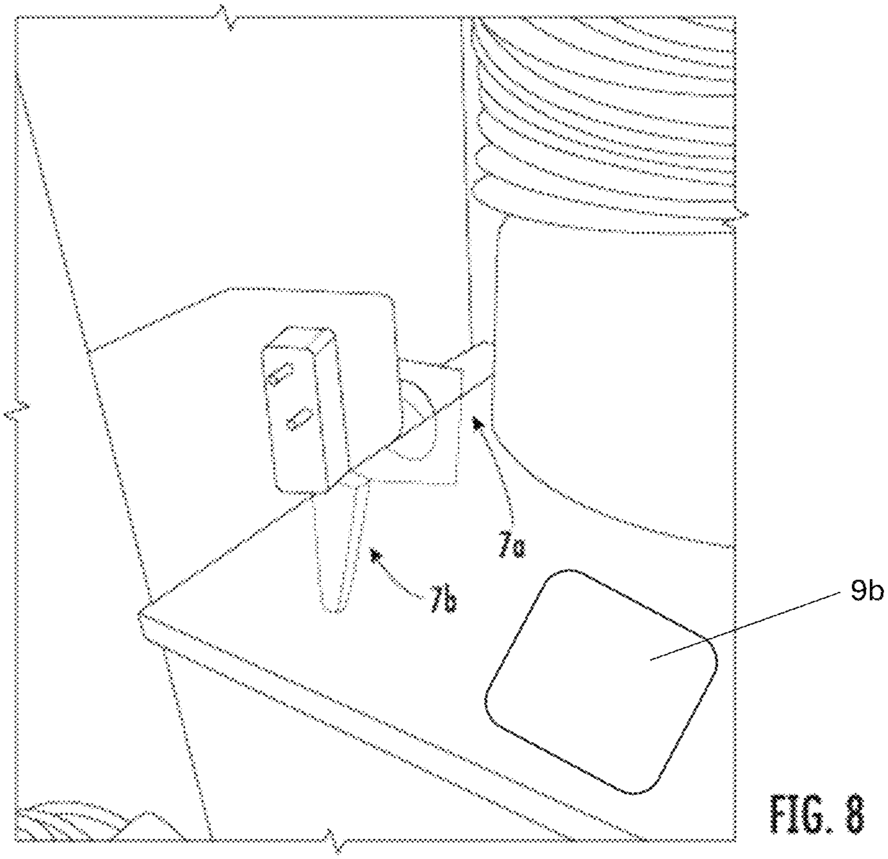
FIG. 8 are views of the bellows drop solenoid and latch of the glove donning apparatus shown in FIG. 1.
Figure 9:
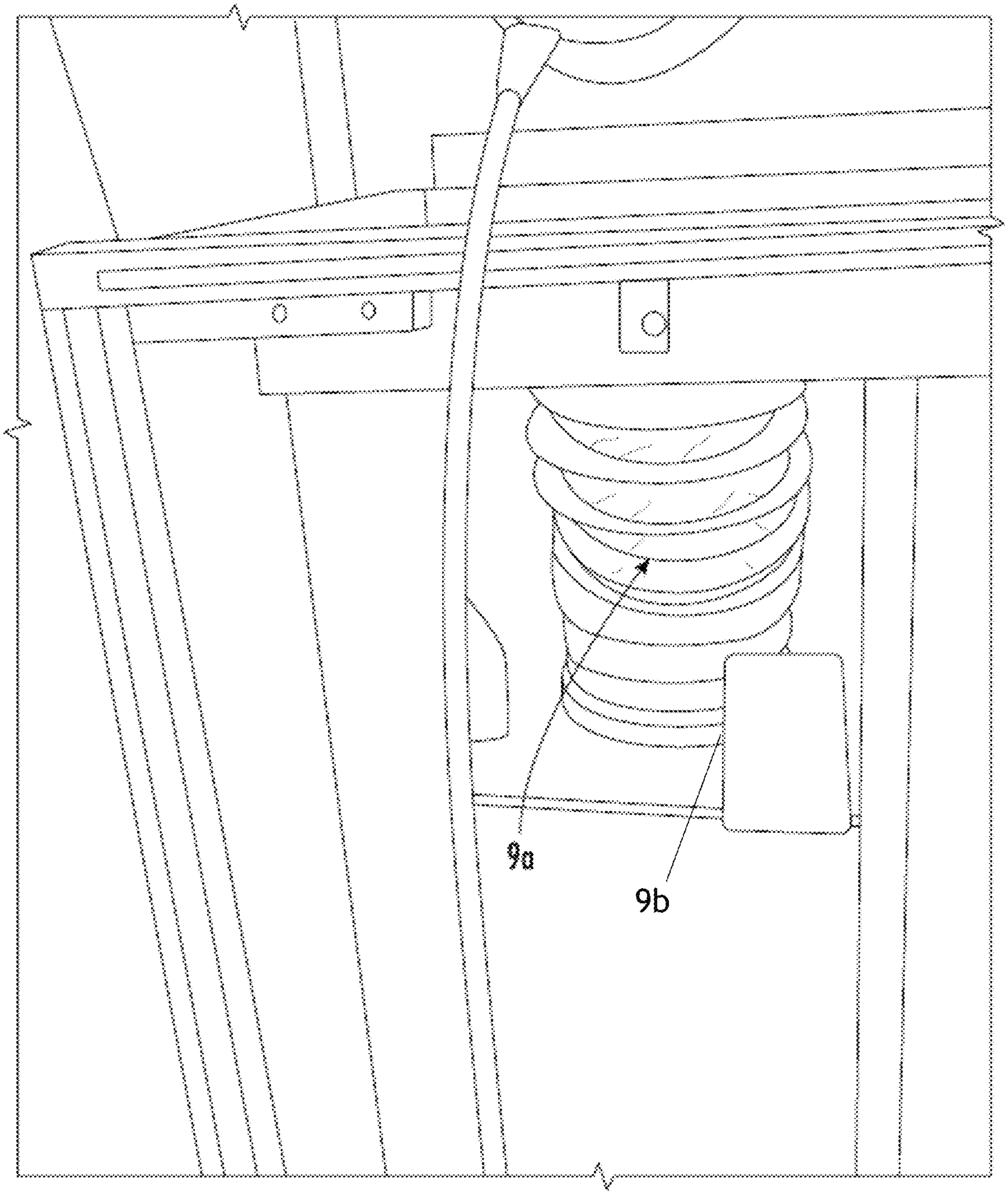
FIG. 9 is a view of the bellows of the glove donning apparatus shown in FIG. 1.
Figure 10:
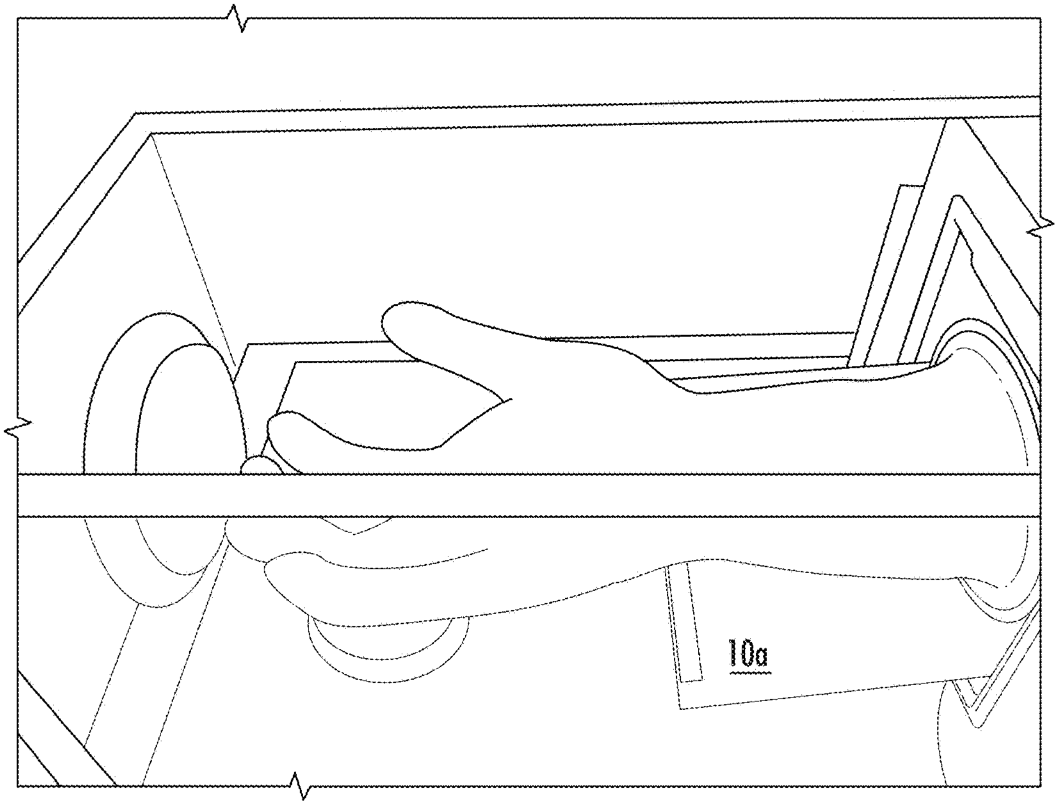
FIG. 10 is a view of an inflated glove of the glove donning apparatus shown in FIG. 1.
Figure 11:
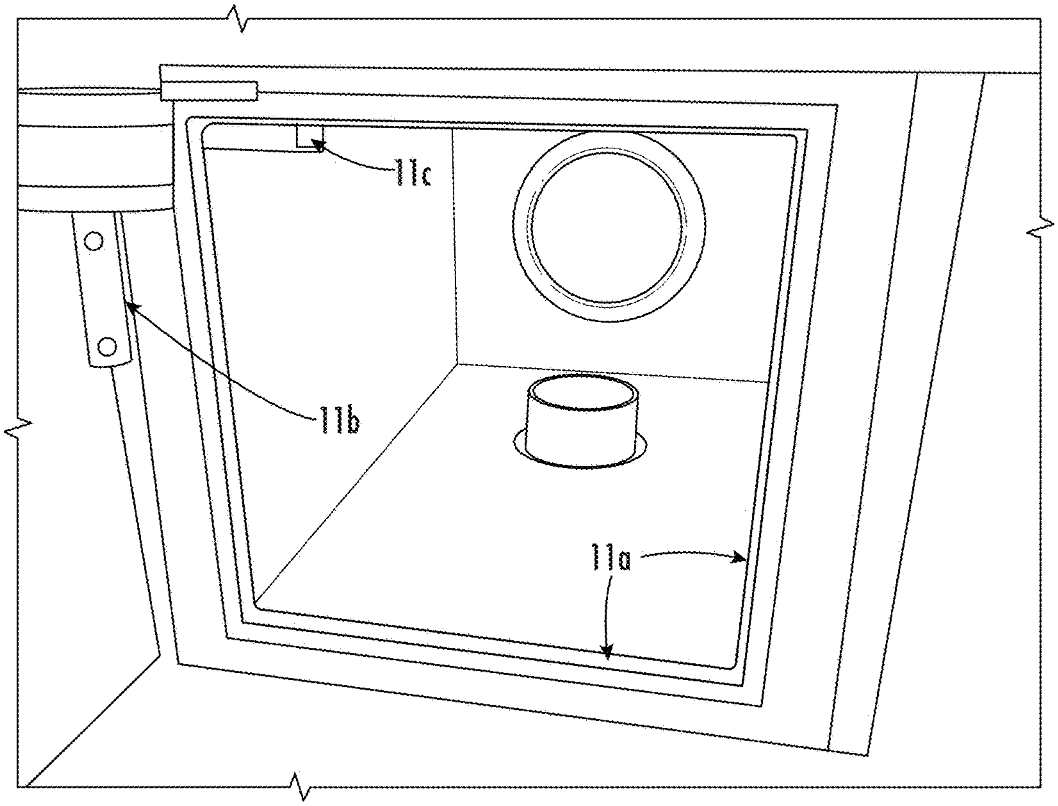
FIG. 11 is a front view of a vacuum chamber box of the glove donning apparatus shown in FIG. 1.
Figure 12:
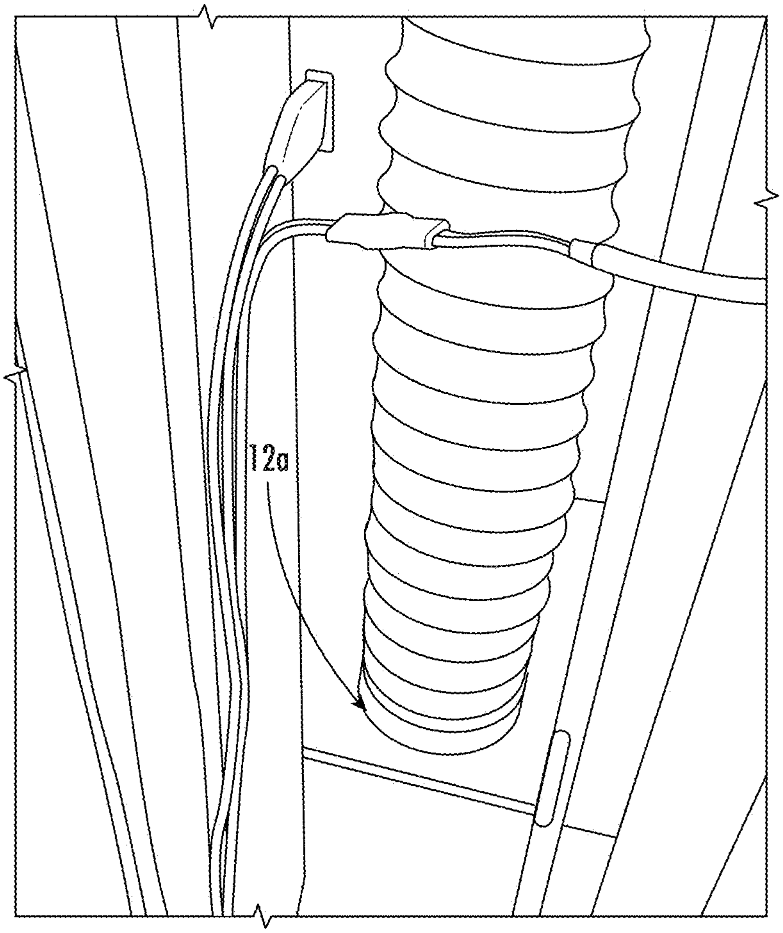
FIG. 12 is a view of the bellows platform of the glove donning apparatus shown in FIG. 1.

The control system then initiates several events. 1. The green lights behind slot walls 1B of each slot of the control panel are turned off. 2. A state of ignoring additional electric eye signals is initiated. 3. Left and Right slides 1C, each packed with a sterile glove or other glove, are moved into position at the open front end of each box. 4. Left and Right solenoids (7A of FIGS. 7 and 8) activate latches (7B of FIGS. 7 and 8) to allow Left and Right Bellows (9A of FIG. 9) to drop, thereby quickly drawing air from the Left and Right vacuum chambers 1E, thereby inflating the Left and Right gloves 10A, of FIG. 10), ready to be donned by the user. 5. Lights are turned on inside the Left and Right buttons 1D, which are inside each box, signaling users to push the buttons 1D, which requires the user to first reach into the inflated gloves 10A. 6. The front doors of each box are opened, allowing the user's hands in. 7. Immediately after the bellows are released, the mechanisms which moved each slide into position, and held the slides in place, may be retracted, reset, or repositioned, since the slides have now been quickly vacuum pulled onto the front walls of the boxes, sealing them against the gasket (11A) to aid in holding the vacuum. When the slide mover mechanisms have been fully retracted or reset, the cartridges of slides advance one position, to align the next slides to the on-deck position.

When the user pushes one of the blue buttons, the controller receives an input signal, and then sends output signals to cause: 1. The blue light in that button to turn off. 2. The cuff release mechanism 11B, such as a rotary solenoid fitted with a lever arm, to cause that glove cuff to be released onto the user's wrist. 3. An electric eye in that box to begin watching for the user's hand to be removed.

When the user pushes the second of the blue buttons, the controller receives a signal, and then signals 1. The blue light in that button to turn off. 2. The cuff release mechanism 11B to cause that glove cuff to be released onto the user's wrist. 3. An electric eye in that box to begin watching for the user's hand to be removed, and also 4. The bellows of both boxes to be reset (detailed later). In another embodiment, each bellows is separately reset as soon as its corresponding blue button is pushed, as the bellows are operated independent of each other. This requires 2 separate lift systems.

When an electric eye signals that the user's hand has been removed from the vacuum chamber 1E, the controller causes that front door to close, and the empty slide to drop though a trap door into a collection bin or collection system underneath.

When both eyes have signaled that the hand has been removed, the controller signals to 1. Re-start watching for signals from the electric eyes of the control panel. 2. Turn on the green lights of the control panel to signal users that the unit is ready for another cycle. 3. Start a "Far-UV" scan inside each box, which irradiates everything inside the box with Far-UV, the 220 nm wavelength germ-killing UV light that is currently under review for human safety by the FDA.

If a user starts a new cycle while the Far-UV scan is in process, the scan would be interrupted, and the donning process would begin again. Alternatively the control panel green lights and readiness state could be delayed until the UV scan is complete. Or either alternative could be made available as an option for users.

In another embodiment, the same mechanism that drives the slide from the cartridge into the donning position, may also drive the empty used slide back into the cartridge clip it came from, before the cartridge is advanced one notch to present a new loaded slide to the on deck position.

In another embodiment, the unit contains gloves of only 1 size, where the slides 1C are already in donning position while the unit is in the resting state, waiting for a user.

In another embodiment, the blue buttons 1D are on the floors of the vacuum chambers 1E, allowing different sized gloves and hands to stretch completely into the gloves and still conveniently push the button with any part of their wrist or hand that is above the button.

In another embodiment, the vacuum lines that draw air from both vacuum chambers join together before connecting to a single bellows, with each vacuum line having a check valve above the coupling where the lines join, to keep a flood of air from one chamber from flooding the other chamber if a user releases one cuff before the other.

In another embodiment, both buttons must be pushed before either cuff is released.

Bellows Fall and Lift System

In one embodiment, bellows drop rapidly at first, quickly hitting a pressure equilibrium between the pull of the vacuum and the tension of the inflated gloves, and then the bellows continue to drop slowly, if any air leaks are in the system. The bellows weight continues pulling the bellows down to make up for any air leakage without deflating the gloves, until finally the cuff is released, flooding the chamber with air, which allows the bellows to drop the rest of the way to the platform 12A. At that point, the lifts, or "elevators" 13A, lift the bellows back into place, ready for the next use again. If the user takes a long time to don the gloves, the bellows will finally land on the platform and the gloves will begin to deflate. In a nearly leak-proof system, the bellows would take a very long time to drop, but the donning process is intended to take only a few seconds.

To adjust the degree of glove inflation, removable weights 9*b* are added to, or subtracted from the base of the bellows to increase or decrease force. An elevator 13A is connected to a drive chain 13B that pushes the elevator 13A up a shaft 13C using rollers 13D rolling in a groove 13E. The elevator lifts the bellows platform 12A with the bellows riding on it, until the bellows platform passes the bellows latch, and then catches on the latch, where it sits in the ready position. The elevator continues its cycle, following the drive chain back down until it hits the button 13F at the base, and the button signals to turn off the motor, and wait for the next cycle. When the bellows latches release again, in the next cycle, the bellows platform immediately drops all the way to the elevator, while the bellows drops quickly to the point of pressure equilibrium, then may slowly drop toward the platform, as air seeps in, then drops quickly again when the glove cuff is released and air floods the vacuum chamber 1E.

Figure 13:
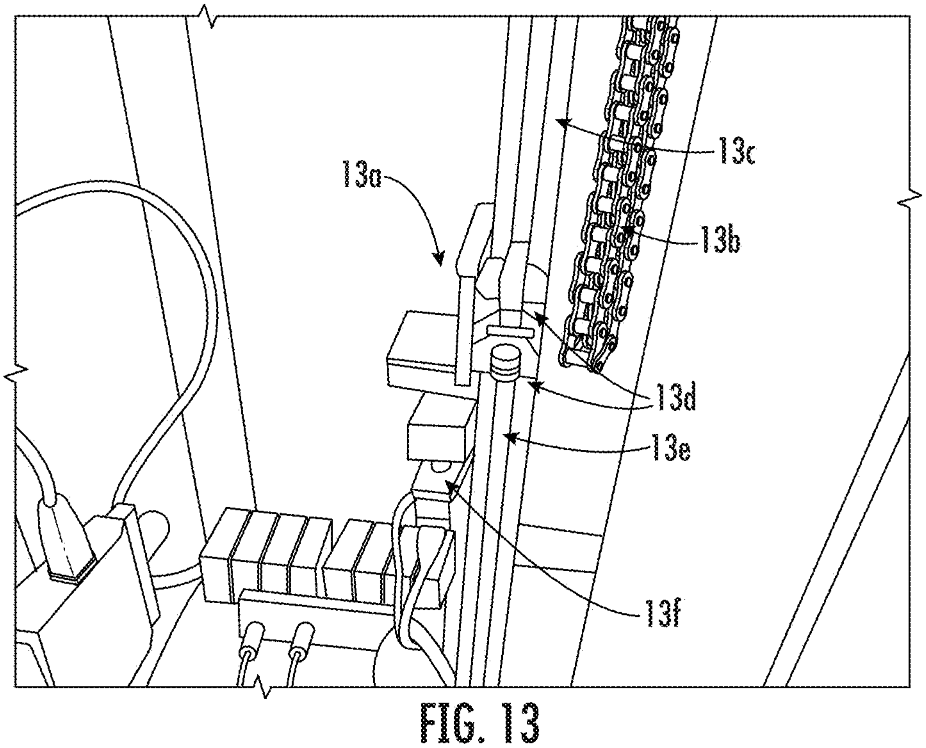
FIG. 13 is a view of the bellows lift system of the glove donning apparatus shown in FIG. 1.
Figure 20A:
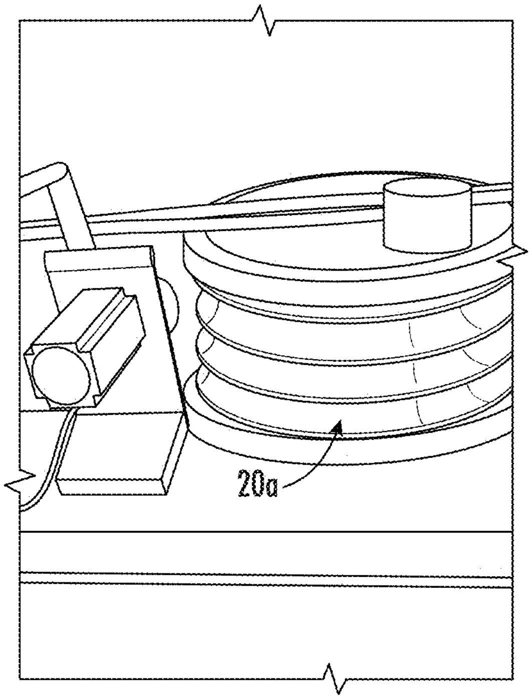
FIG. 20A is a view of an embodiment of the bellows of the glove donning apparatus shown in the extended position.
Figure 20B:
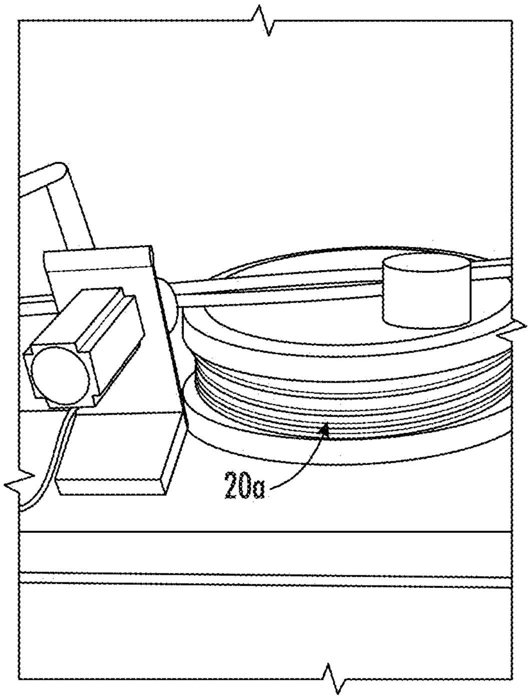
FIG. 20B is a view of an embodiment of the bellows of the glove donning apparatus shown in the compressed position.

In another embodiment, shown in FIGS. 20A and 20B, large diameter bellows 20A take less vertical space, also drops by gravity, but the elevator is raised and lowered by a cam driven by a motor, removing the need for some elements in FIG. 13. In another embodiment, bellows are mechanically pulled or pushed open, and then mechanically made to continue pulling out any air leaks.

Cuff Release Mechanism

Figure 14:
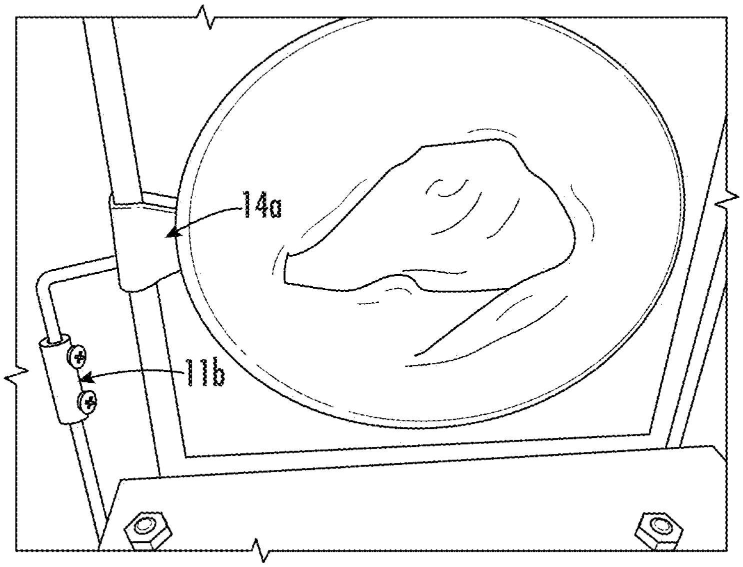
FIG. 14 and FIG. 15 and FIG. 16 are views of cuff release system of the glove donning apparatus shown in FIG. 1.
Figure 15:
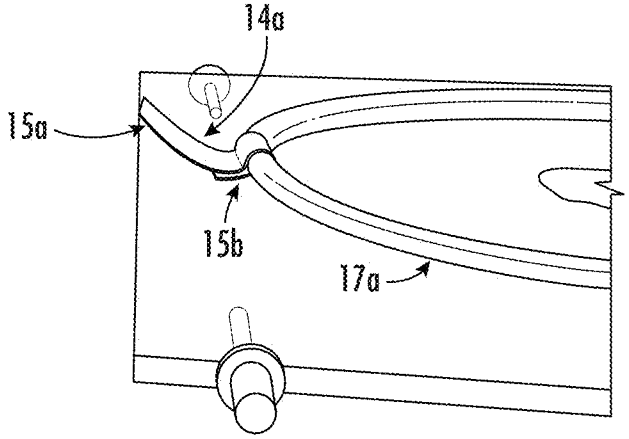
Figure 16:
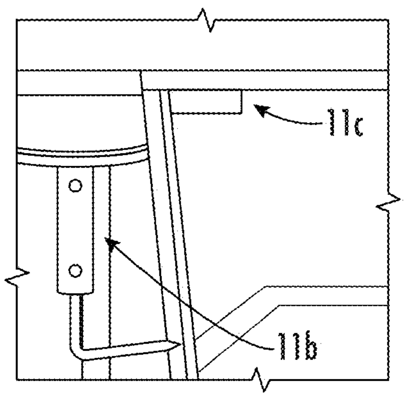

When the blue button is pushed, it turns off the blue light, and the cuff release mechanism 11B, shown in FIG. 14, pushes out the cuff release tab 14A, thus levering the glove cuff upward, causing the glove cuff to come off the cuff ring 17A at that point. Then the elasticity of the glove and pressure from the inserted, forward positioned hand, causes the glove cuff to release quickly all the way around the cuff ring. As shown in FIG. 15, the tab 14A is attached to and hinges from the cuff ring 17A, and shaped, as shown by shape of the tab profile 15B, to roughly match the profile of the cuff ring 17A, but also extended, as shown by the tab lever extension 15A to engage the cuff release mechanism 11B. This works well, but if a user is particularly aggressive, there may be times when the glove cuff can pull off the cuff ring before the blue button is pushed. In another embodiment, shown in FIGS. 27 and 28, instead of a tab, there is a separate ring, a releasing ring 27D, which may be made of a stiff, but somewhat flexible metal that would encircle the cuff ring, and hug it when the releasing ring is in its relaxed position 27A.

Figure 27:
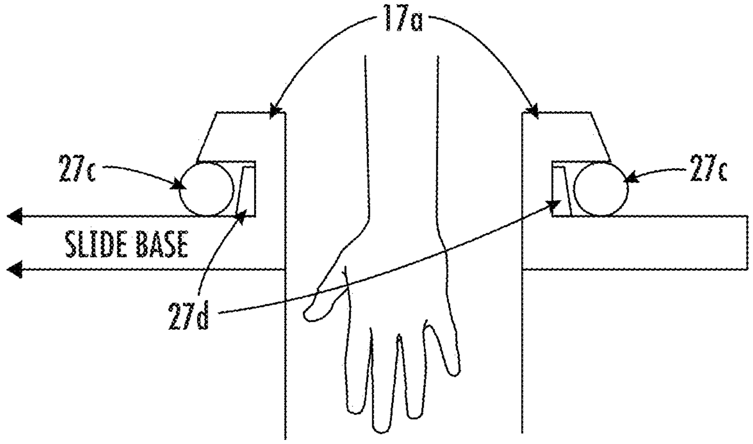
FIG. 27 and FIG. 28 are views of a releasing ring system for slides of the glove donning apparatus shown in FIG. 1.
Figure 28:
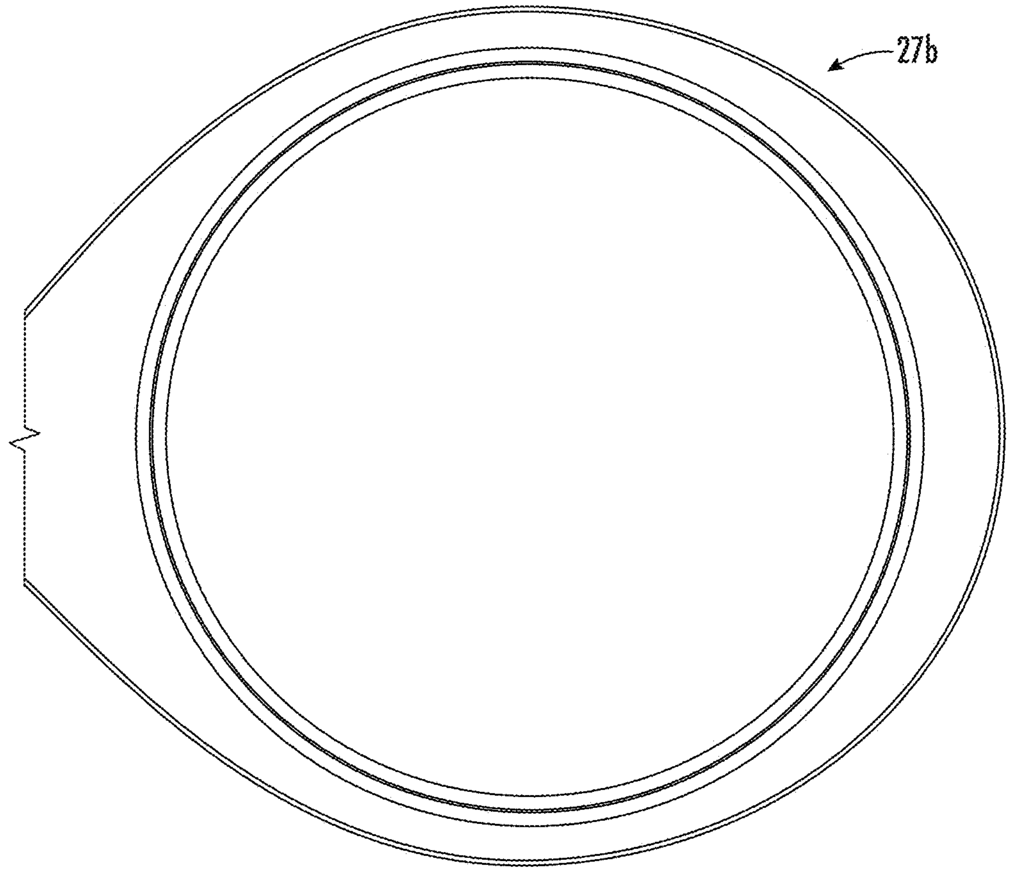

In another embodiment, shown in FIGS. 27 and 28, instead of a tab, there is a separate ring, a cinched releasing ring 27D, which may be made of a stiff, but somewhat flexible metal that encircles the cuff ring 17A, and hugs it when the releasing ring 27D is in its cinched position, as shown in FIG. 27. The cinched releasing ring 27D is then released to its open position, becoming the open release ring 27B shown in FIG. 28, which has moved out and away from the cuff ring 17A which pushes the glove cuff, shown as 27C in FIG. 27 into a position where it releases. This allows a more aggressive initial engagement of the glove cuff to the cuff ring 17A, which minimizes accidental cuff release. This initial aggressive engagement is achieved by making the cuff ring 17A taller, and with a deeper groove, so the glove cuff tucks farther under the lip, and is therefore harder to accidentally release. In FIG. 27, the cuff ring 17A is shown molded into the slide, all as one part.

Figure 17:
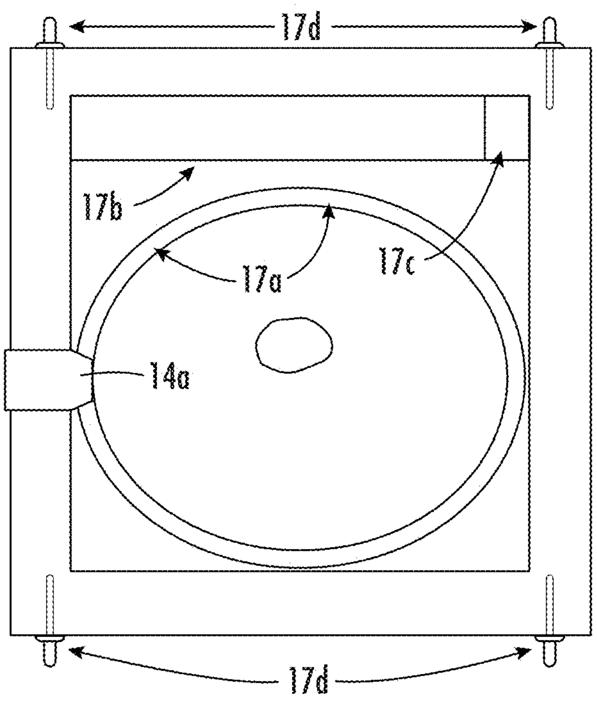
FIG. 17 and FIG. 18 are views of a slide of the glove donning apparatus shown in FIG. 1.
Figure 18:
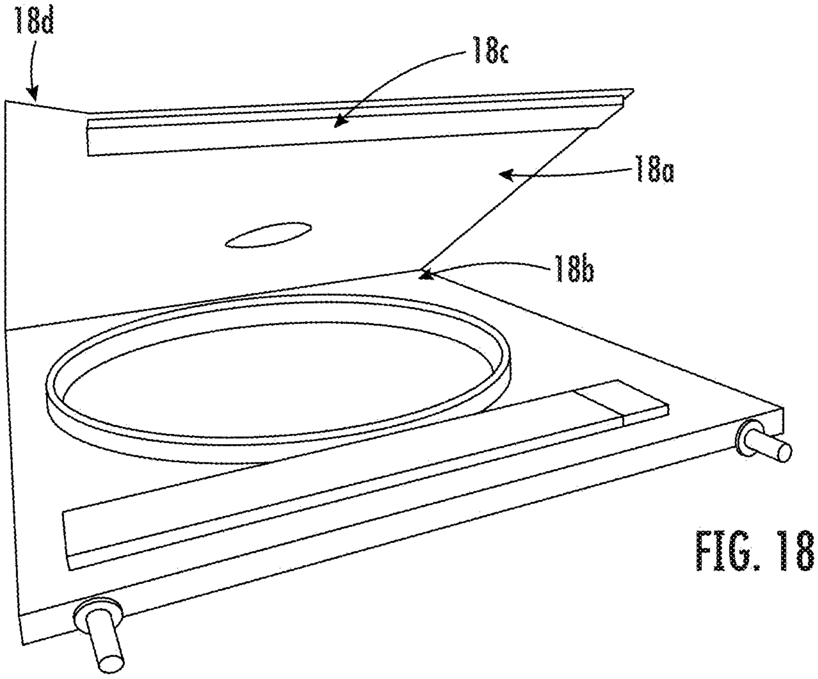
Figure 19:
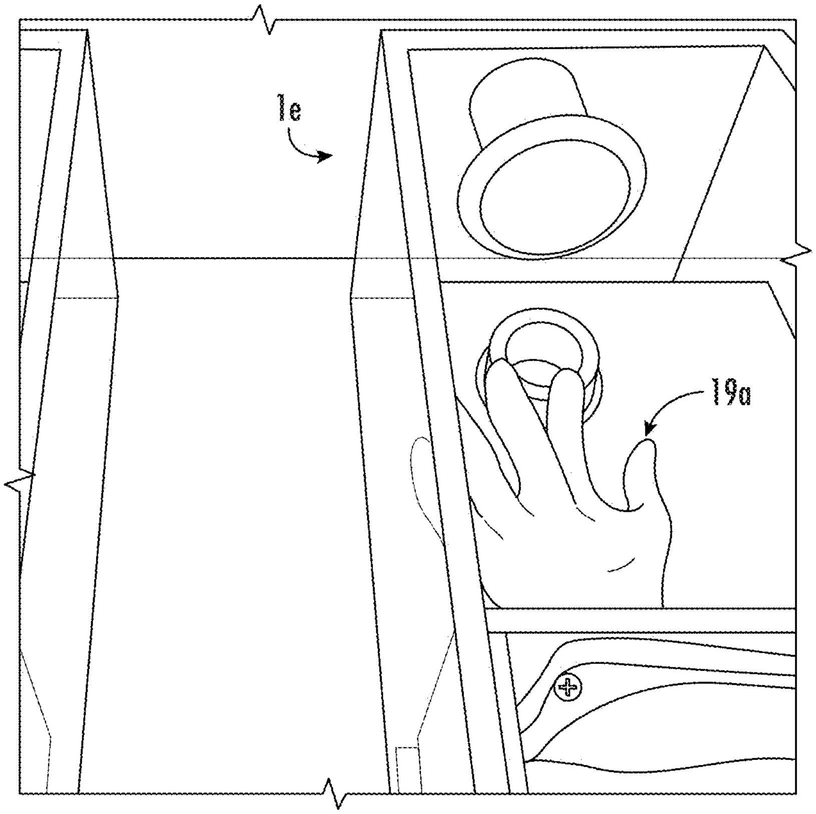
FIG. 19 is a view of a glove unfurled into a vacuum chamber of the glove donning apparatus shown in FIG. 1.

Slides may be made of polycarbonate or other materials, and may include components shown in FIGS. 17 and 18: a cuff ring 17A for mounting the cuff of a glove, a cuff release tab 14A, a hinged flap 18A for retaining a furled glove, a magnetic strip 17B along the top of the slide, which engages the ferrous strip 18C along the top of the flap. In another embodiment, the ferrous & magnet positions are switched. The slide also includes a dog ear 18D on one top end of the flap 18A, to cause the flap 18A to open, as described below. The slide also includes a small piece of non-ferrous material, part 17C to help break the magnet pull at the tip, when the ferrous strip 18C is pulled off the magnetic strip 17B. Part 17C can be injection molded as part of the slide itself. The slide also includes guide shafts 17D near each corner, as described below. As the slides are pushed into position, the flap protrusions 11C push on the dog-ear 18D and wedge open each flap 18A that retains the furled gloves in the slides, by wedging the ferrous strip 18C away from the magnetic strip 17B, causing the flap 18A to quickly drop completely open, from the wedging momentum and gravity, allowing the gloves to unfurl into the vacuum chamber 1E. The gloves may unfurl completely or incompletely, but they are free to inflate with no encumbrances. Unfurled glove 19A is shown in FIG. 19 inside vacuum chamber 1E.

Figure 21:
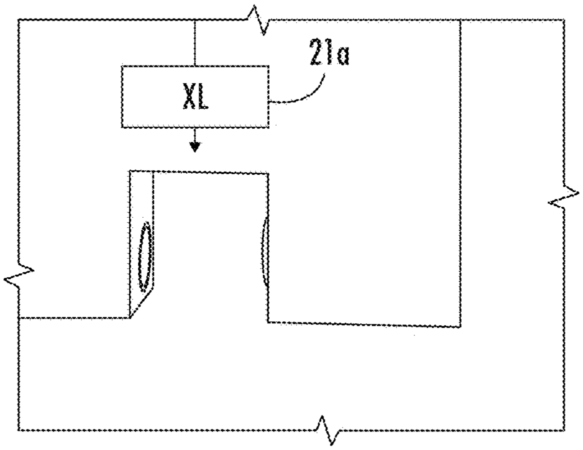
FIG. 21 is view of a control panel label of the glove donning apparatus shown in FIG. 1.
Figure 22A:
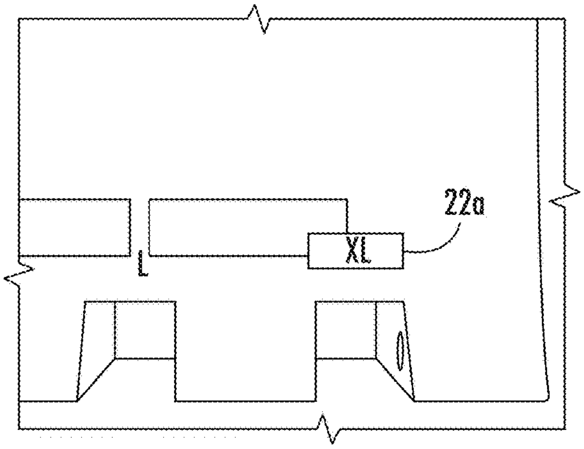
FIG. 22A and FIG. 22B and FIG. 22C are views of a control panel label screen of the glove donning apparatus shown in FIG. 1.
Figure 22B:
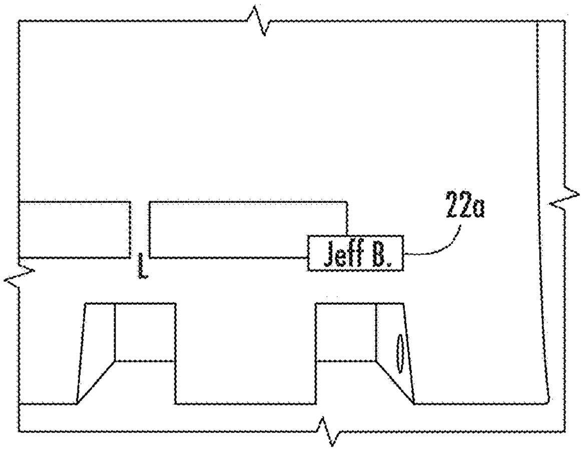
Figure 22C:
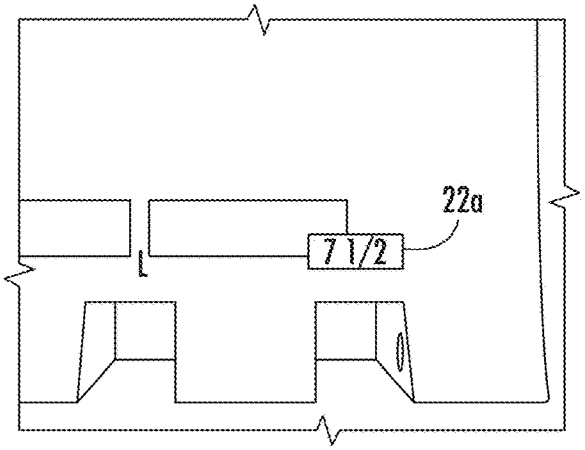

The embodiment modeled in FIG. 1 has control panel options S, M, L, XL, so this embodiment has 4 cartridges having those 4 different glove sizes. But users might want to choose different sizes or different types of gloves, which can easily be done by loading the unit with cartridges containing the desired gloves, and changing the labels 21A on the control panel (FIG. 21). One embodiment has frame slots for different labels to fit in. Another embodiment has small screens 22A displaying whatever label the user enters, as represented by FIGS. 22A, 22B, 22C. Users may change the displays on the website or the app, which, via wireless, changes the label on the unit, and automatically orders a technician to change the cartridges for you.

Figure 23:
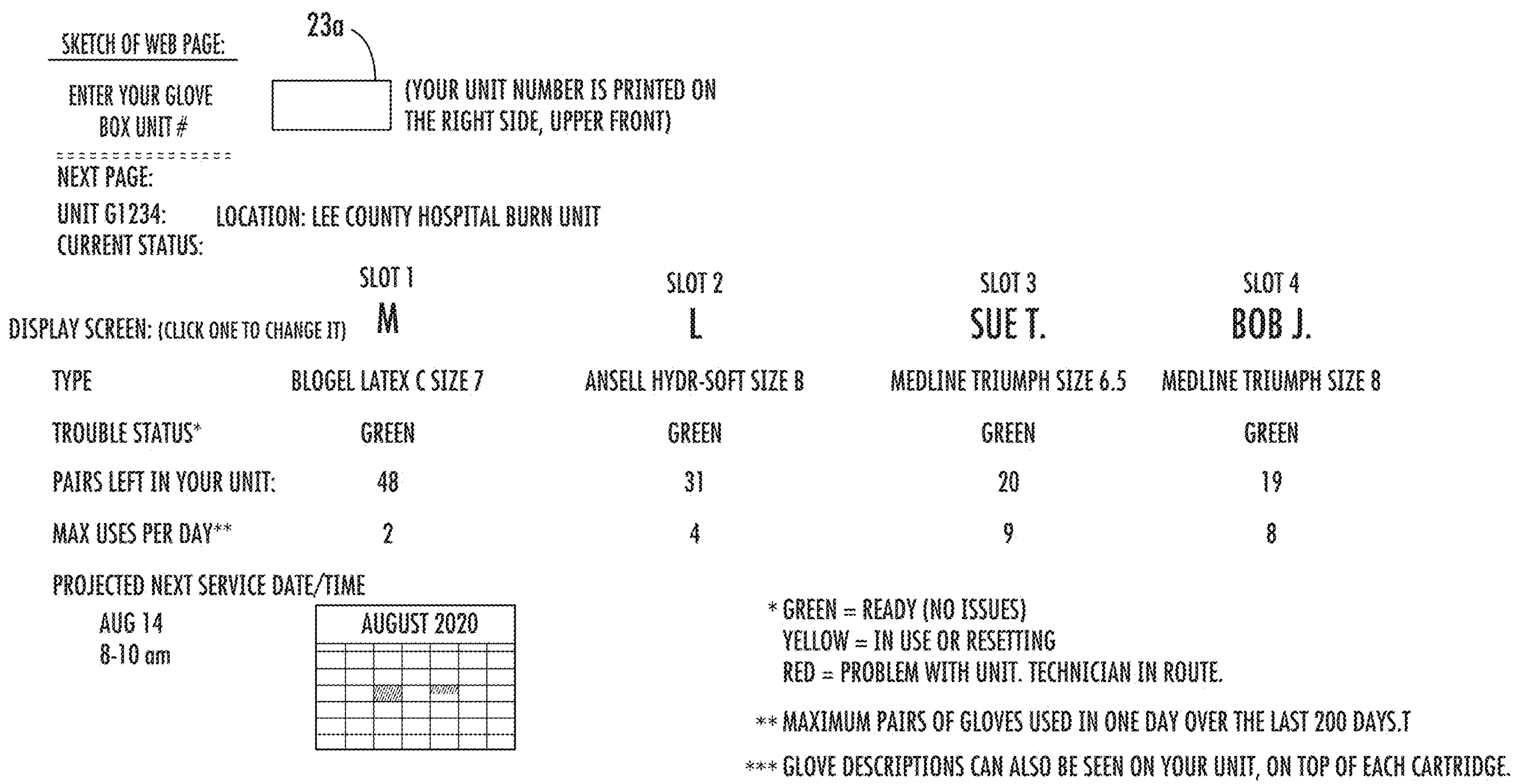
FIG. 23 is a view of an embodiment of a webpage for the glove donning apparatus shown in FIG. 1.

FIG. 23 models one embodiment of the website. Customers input their unit number into the form box 23A, and the information shows the current stock of gloves in the unit, and the next scheduled restocking or service call, calculated with usage assumptions input by technicians and/or based on usage history reported by the unit itself. Customers could make service requests, change the unit screen displays, order different gloves to be stocked, and other actions.

The current glove donning apparatus can also be made to work with medical exam gloves that are non-sterile. This might be an even better application, since some exam rooms see a lot of glove use. The staff might change gloves more appropriately if it's easier, and the gloves might be cleaner if the boxes aren't open to the air all day, and being handled by lots of different people.

In another embodiment, each hand swipe slot 1A lights yellow if a problem is detected or the unit runs out of gloves for that particular size. In that case, the unit signals via Wi-Fi or cellular or some other way to notify the home server, and an algorithm would determine if the issue could be addressed remotely or if a service call is needed. Similarly, an inventory system sends updates to the server after each use, or after a certain number of uses, or each day, hour or some other period of time. The service algorithm uses this information in scheduling service calls for maintenance and empty cartridge replacement.

Slide Mover Mechanism

Figure 24:
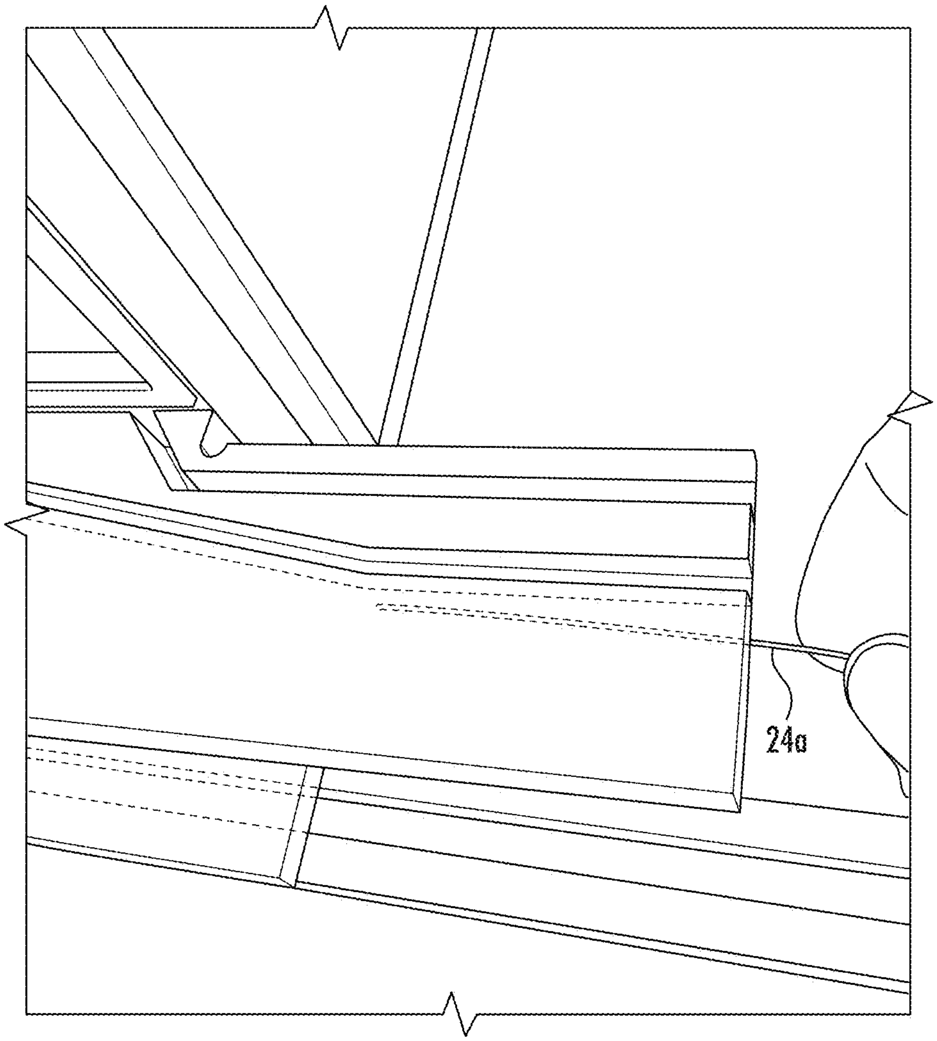
FIG. 24 and FIG. 25 are views of a cable slide driver system of the glove donning apparatus shown in FIG. 1.
Figure 29:
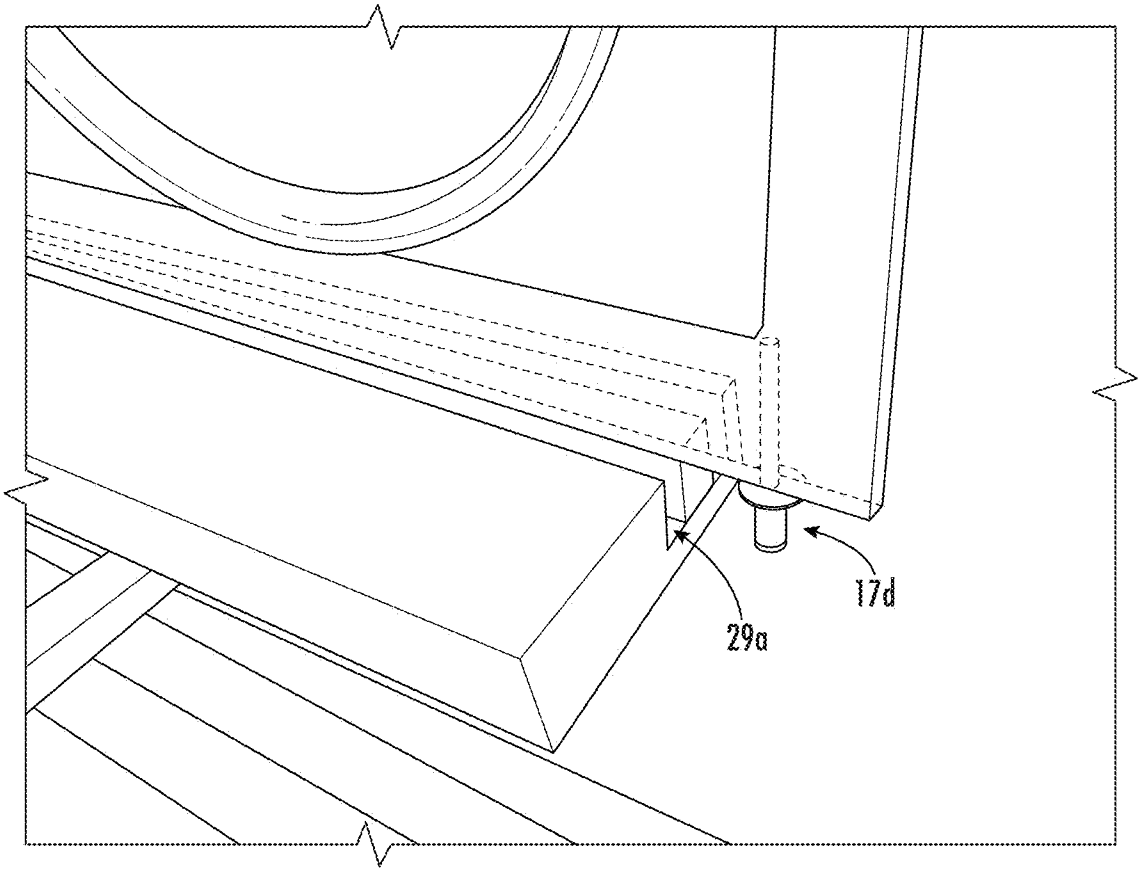
FIG. 29 is a view of the pin and groove slide guide system of the glove donning apparatus shown in FIG. 1.

Looking closer at the slides in FIG. 29, there are 4 shafts or pins 17D protruding, one near each corner, of a slide and these ride inside slide track grooves 29A that guide the slides into position. In this embodiment, the slides generally come in from the sides, but also slightly from the front to minimize rubbing the slide against the vacuum seal gasket 11A. There are several ways to move the slides from the on-deck position into place against the front opening gasket ready for glove inflation. One embodiment uses small cables that push through tunnels underneath the guide tracks that push the slides' corner pins along the tracks, where the lower cable 24A is underneath the surface in a tunnel that is shaped to loosely fit the cable (FIG. 24). The tunnel follows right under each track, and is slotted open to the track above it, allowing a slide pin 17D to extend down into the cable tunnel, where the end of the cable will engage the pin near its bottom end, and push it along. The cable is flexible, and is rolled up on a spindle attached to a motor, and the spindle has an adjacent physical restriction which forces the cable along only one possible path as it is unreeled: into the tunnel. The motor and spindle would quickly unreel the cable when the controller signals for a new slide.

Figure 25:
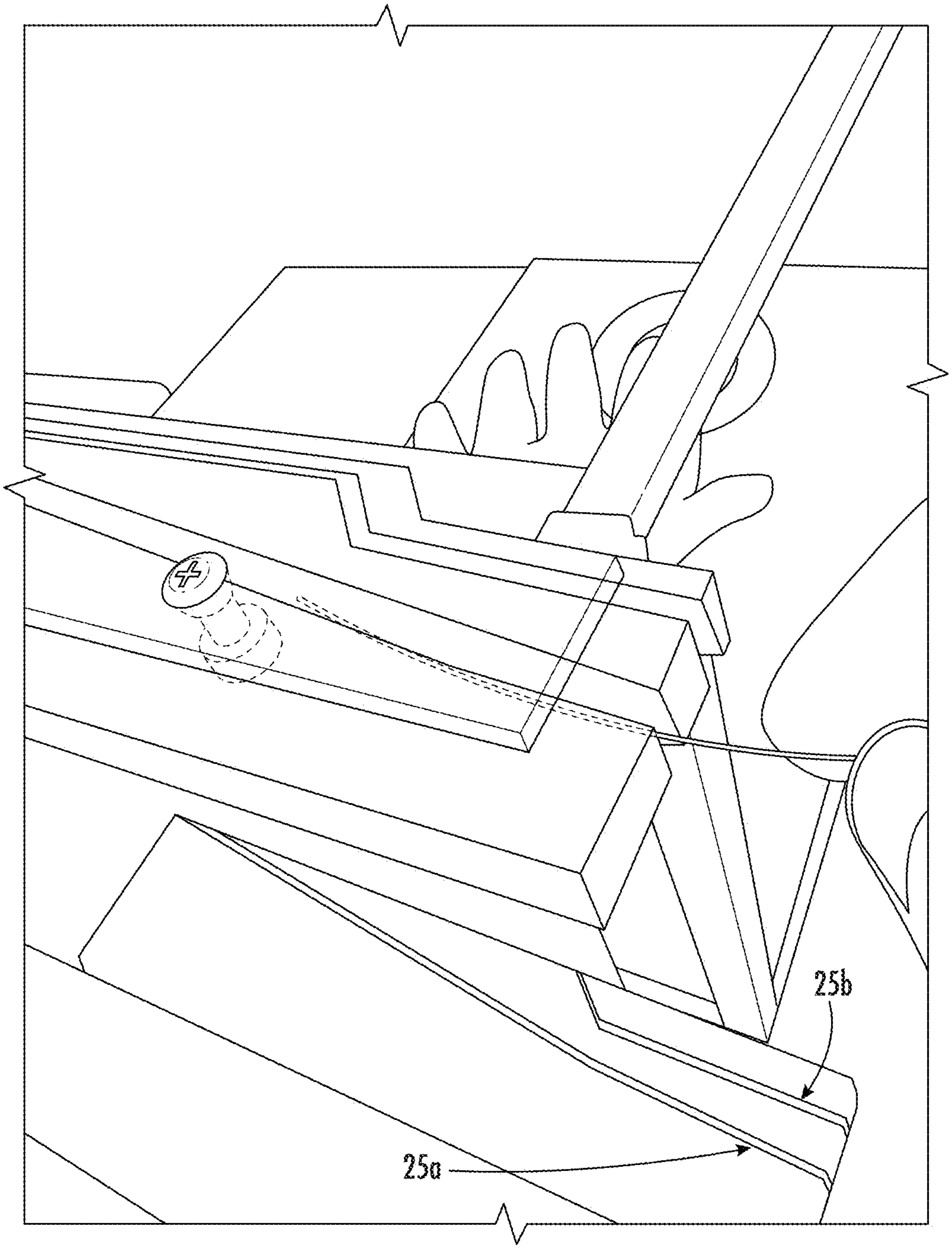

The top cable 25*c*, of FIG. 25, uses the same design to push the slide's top pin. Likewise, it is routed through a tunnel right above, and connected to the top pin track. So the top and bottom pins of a slide are pushed along simultaneously with 2 separate cables, leading from the same spindle. The spindle may be located anywhere inside the unit, since cable sleeves could be used to route the cables to the positions needed, similar to sleeved cables used in bicycle gear shifting. The cables could also be left fully extended until the bellows have dropped, which could aid in holding the slide in place against the vacuum seal.

In other embodiments, a slide driver is mounted to a timing belt or screw drive to effect the necessary movement.

Figure 26:
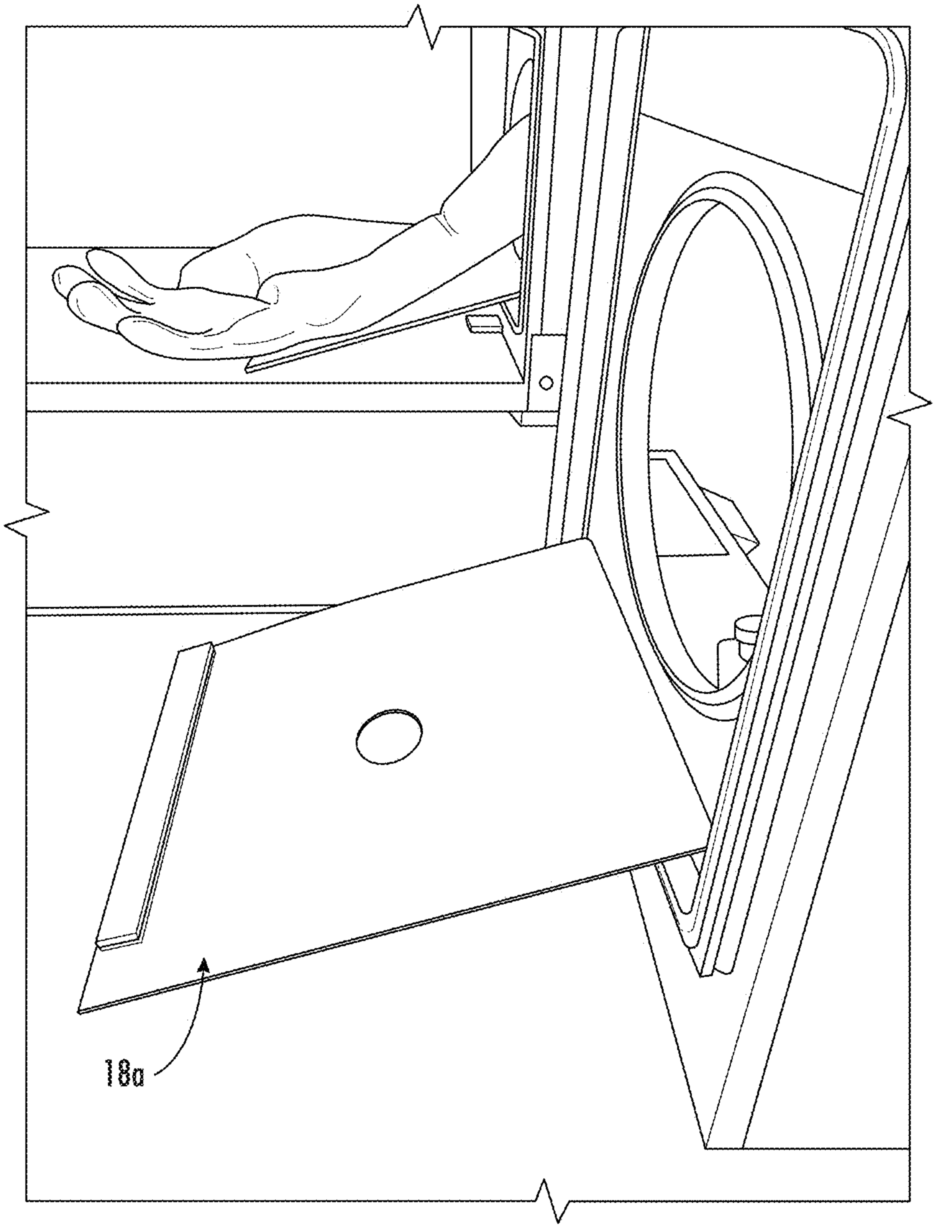
FIG. 26 is a view of a slide flap opened into a vacuum chamber of the glove donning apparatus shown in FIG. 1.
Figure 30A:
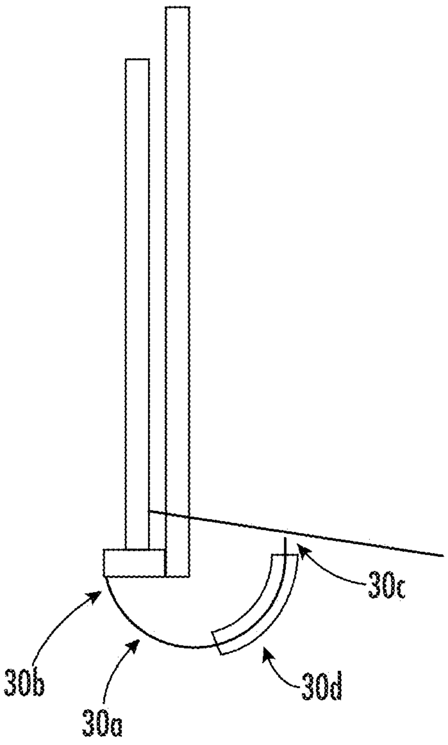
FIG. 30A is view of the slide flap closing mechanism of the glove donning apparatus shown in FIG. 1 in a first position.
Figure 30B:
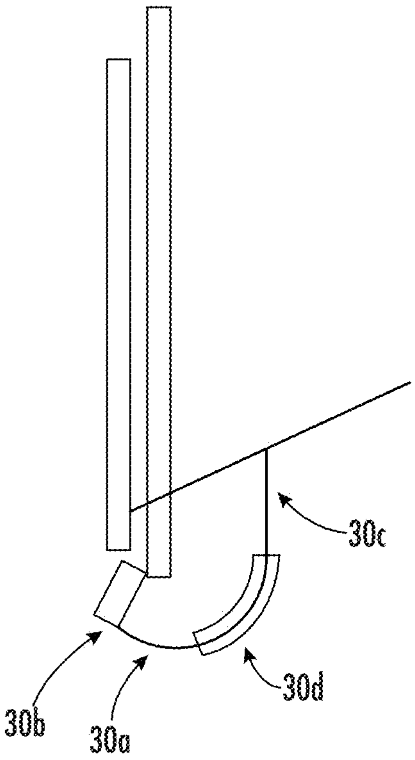
FIG. 30B is view of the slide flap closing mechanism of the glove donning apparatus shown in FIG. 1 in a second position.

When the trap door opens to let the slide fall into the collection bin, its fall is somewhat hindered by the slide flap 18A being open, not allowing the slide to fall through the trap door as shown in FIG. 26. In one embodiment shown in FIGS. 42 and 43, the trap door 42B has a stiff curved wire 42D attached under its front edge, and extending back and under and up through a hole in the bottom of the vacuum chamber 1E, where the other end of wire 42D is in position to push the flap 18A up. In a similar embodiment, depicted in FIGS. 30A and 30B, the wire is replaced by a cable 30A (with ends 30B and 30C), which cable 30A extends through a sleeve 30D to guide it and aid its movement.

When the trap door is opened, either by mechanically applied force, or by gravity, or both, the cable or wire is pushed down on the front end, thereby pushing the cable up on the other end, which pushes the flap 18A up. The flap 18A can be pushed with enough force to finish closing on its own momentum. The flap-opening protrusion 11C does not hinder the flap 18A closing, as the slide falls below the protrusion 11C.

Cartridges

Figure 31:
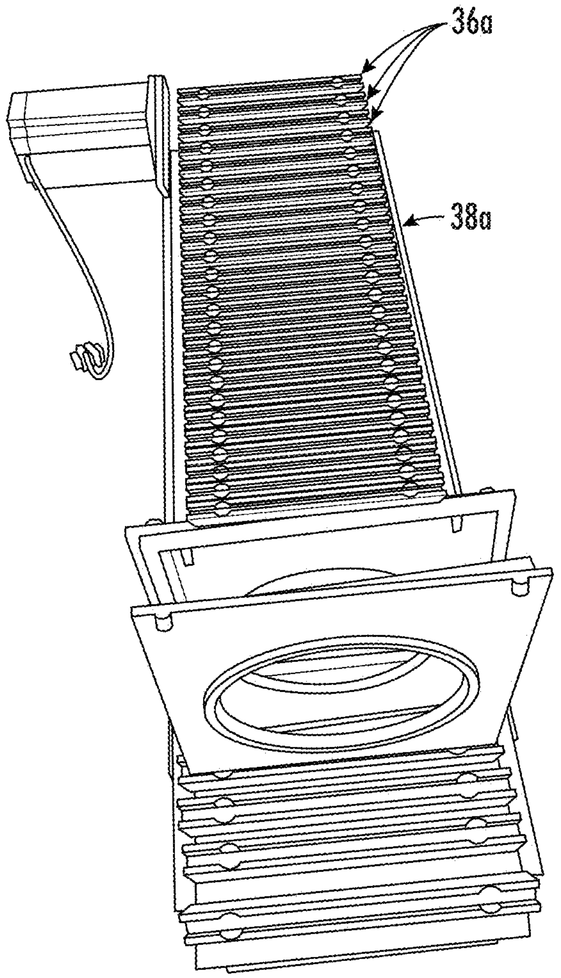
FIG. 31 is view of slides loaded into a cartridge of the glove donning apparatus shown in FIG. 1.

In one embodiment, a timing belt or belts 38*a* of FIG. 31, have multiple slide clips 36*a*, loaded with slides, each containing a glove. The cartridge advances the next slide after each use, by turning the pulley with a motor. The slides may only be loaded on one side of the timing belt, so the slides all stick out in one direction as shown in FIG. 31. As such, 2 cartridges could be loaded on each side of each glove box, allowing up to 4 selections for users, which allows the S, M, L, XL selections on the control panel in FIG. 1.

Figure 38:
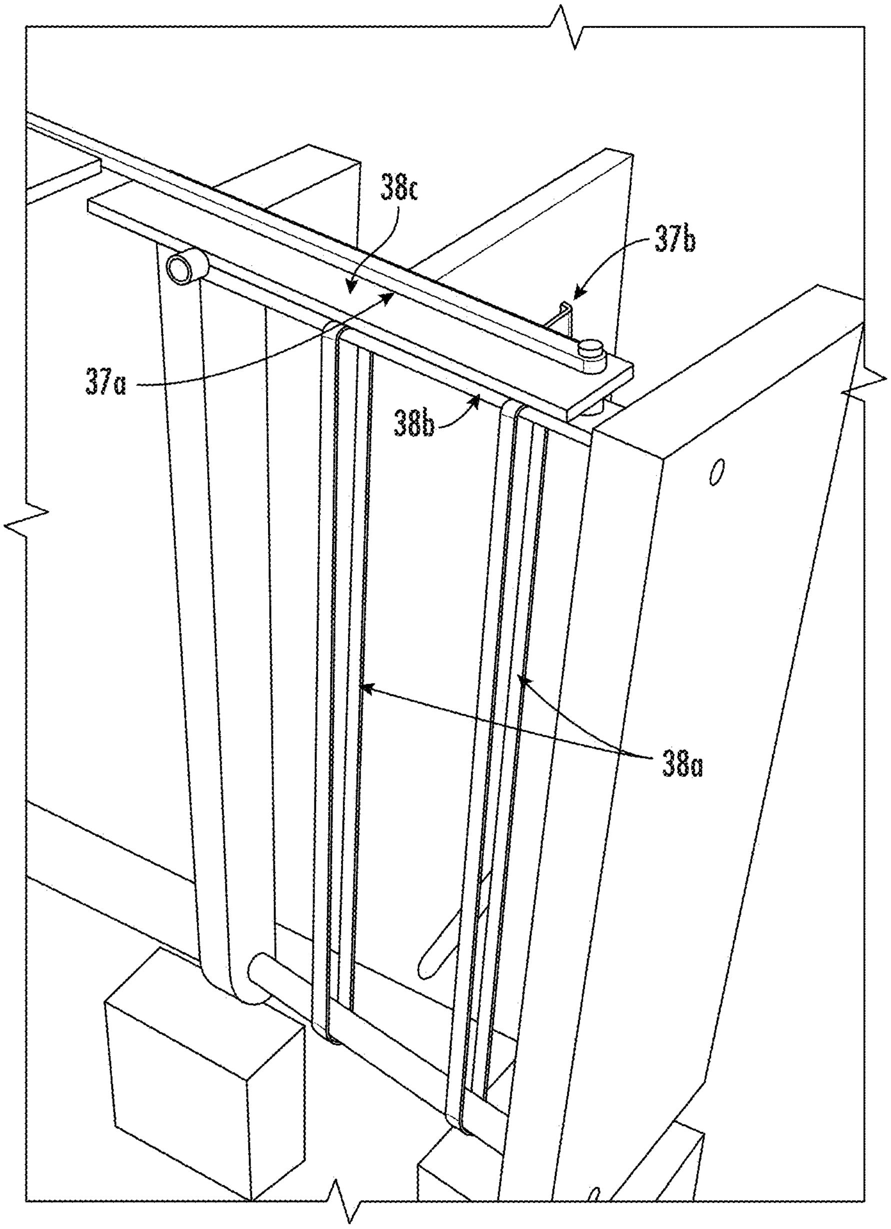
FIG. 38 is a view of a cartridge aligned with the slide drive and guiding systems of the glove donning apparatus shown in FIG. 1.

As shown in FIG. 38, as a slide nears the top, the timing belt(s) 38*a* turns the sharp radius along the top pulley 38*b*, and flips the slide into position against a backstop 38*c*, where it is ready to be pushed through the tracks into the glove box. In one embodiment, the clip automatically opens, due to the belt stretching outward while rounding the pulley, thereby unclamping the slide from the timing belt. Another embodiment, shown in FIG. 34, has clips 36*a* that serve as the first section of bottom slide track. In this embodiment, the slides fit the clips 36*a* more loosely, and are held in the clips 36*a* by the walls of the cartridge, instead of being clamped in place by tight fitting clips.

Another embodiment has a clean-procedure for restocking and maintaining the units, and a sterile procedure for the sterile glove units. Before leaving the warehouse, the server tells the technician which cartridges to stock on his rolling supply cart, and even which cartridges to stack on top, and also the route to take from one unit to the next, such that the correct cartridge is always at his/her fingertips. He/she then collects the empty cartridges and slides, performs any maintenance due (again, as indicated by the server), then restocks, and tests the unit, before moving to the next unit that needs service.

In another embodiment, the units are powered by batteries, and the service cart has charged batteries, for the technician to replace drained batteries on the unit. The cart has slots for the batteries to electrically connect to a circuit within the cart, such that the cart, when later plugged into its position in the delivery truck becomes a charging center for all the batteries plugged into it. The truck itself may also be all electric to facilitate this recharging.

Another embodiment uses a scanner into which users insert their hands to get recommended sizes to try, since some glove companies have begun considering various new shapes and sizes to accommodate more of the many different hand types. Other products currently exist that scan solid parts for the purpose of creating CAD files that can be used to reproduce the scanned parts. In this embodiment, these products or others are adapted to make a hand scanner as described for this purpose.

Figure 32:
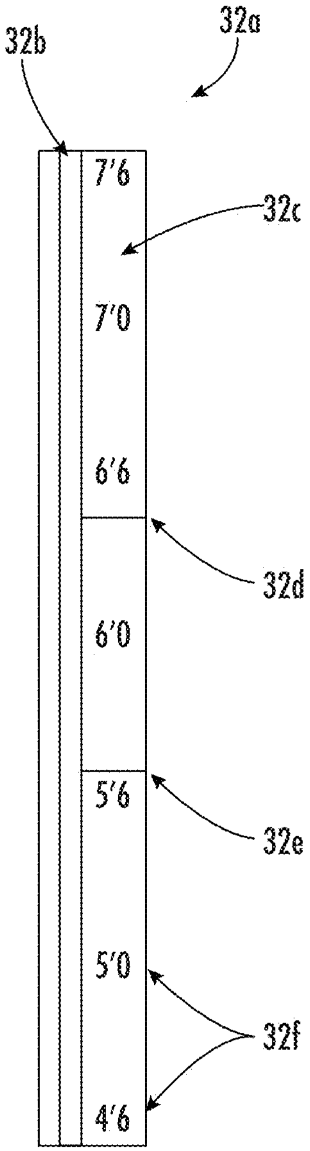
FIG. 32 is a view of a touchless wall mounted control bar of another embodiment.

Other embodiments include wall mounted units and ceiling mounted units, in addition to the floor models. Space is tight in many hospital rooms, and ceiling mounted units need to be raised out of the way when not in use. FIG. 32 models a touchless wall mounted control bar 32*a* for the ceiling model, which includes a scaled indicator strip 32*c*, with a cross-hatch 32*d* indicating the current height of the bottom of the glove box unit. The scale might go from 4'6" to 7'6", although the control bar itself may be 12" or less.

To adjust the height, the user swipes fingers through the finger swipe slot 32*b*. Starting where the cross-hatch 32*d* is, and raises or lowers their hand to the position desired, exemplified here by destination height line 32*e*. Upon initiating this swipe, the 2nd cross-hatch appears, rapidly tracking the user's hand position, the user slides to the height desired on the scaled indicator strip 32*c* and withdraws the hand. The hanging ceiling unit immediately starts adjusting its height to that point, while the original cross-hatch continually tracks and displays the current position, as it continues to raise or lower, until it reaches the desired point, where the hanging unit stops adjusting, and the 1st cross-hatch merges with the 2nd cross-hatch. Then the 2nd cross-hatch disappears, leaving the 1st cross-hatch still indicating the current position. Now the user can see if the height seems right, and can easily adjust it again if needed, using the same method.

Front Door

Figure 33A:
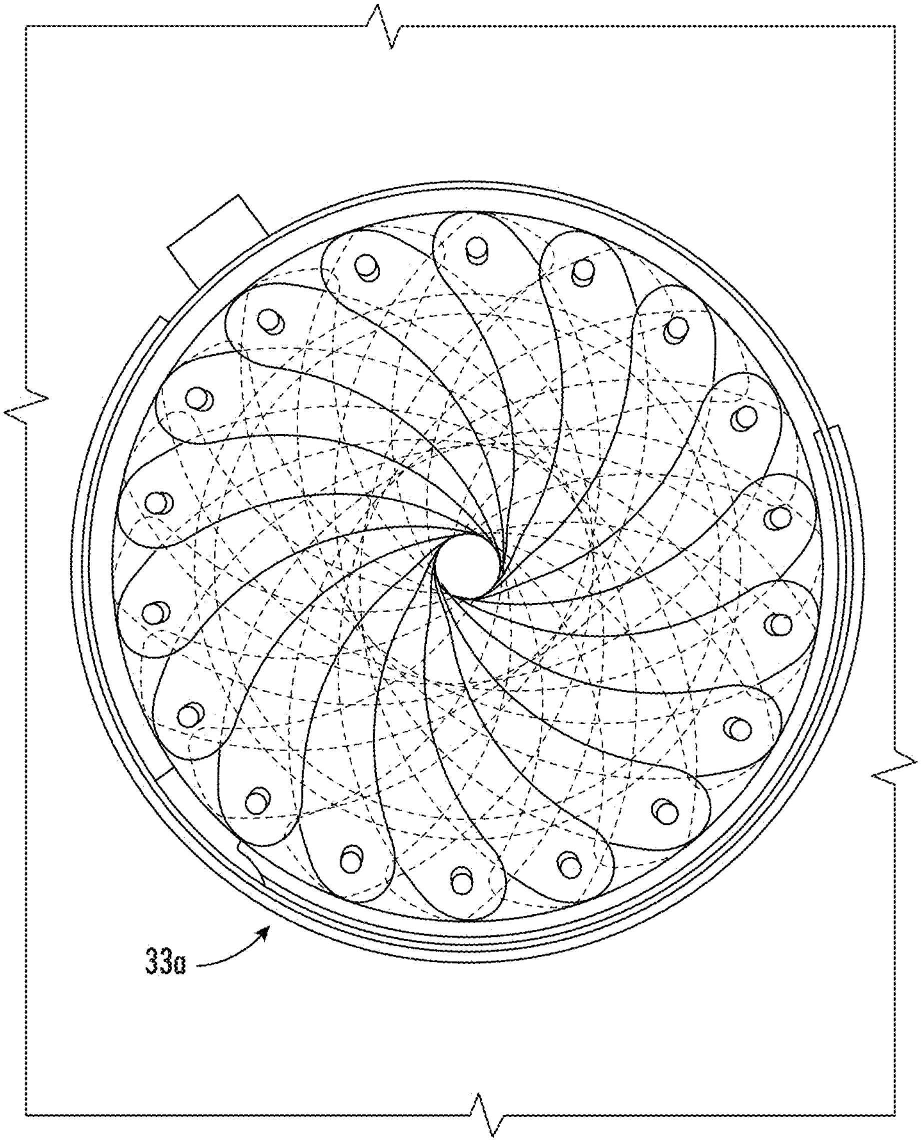
FIG. 33A and FIG. 33B are views of an iris hand door of another embodiment.
Figure 33B:
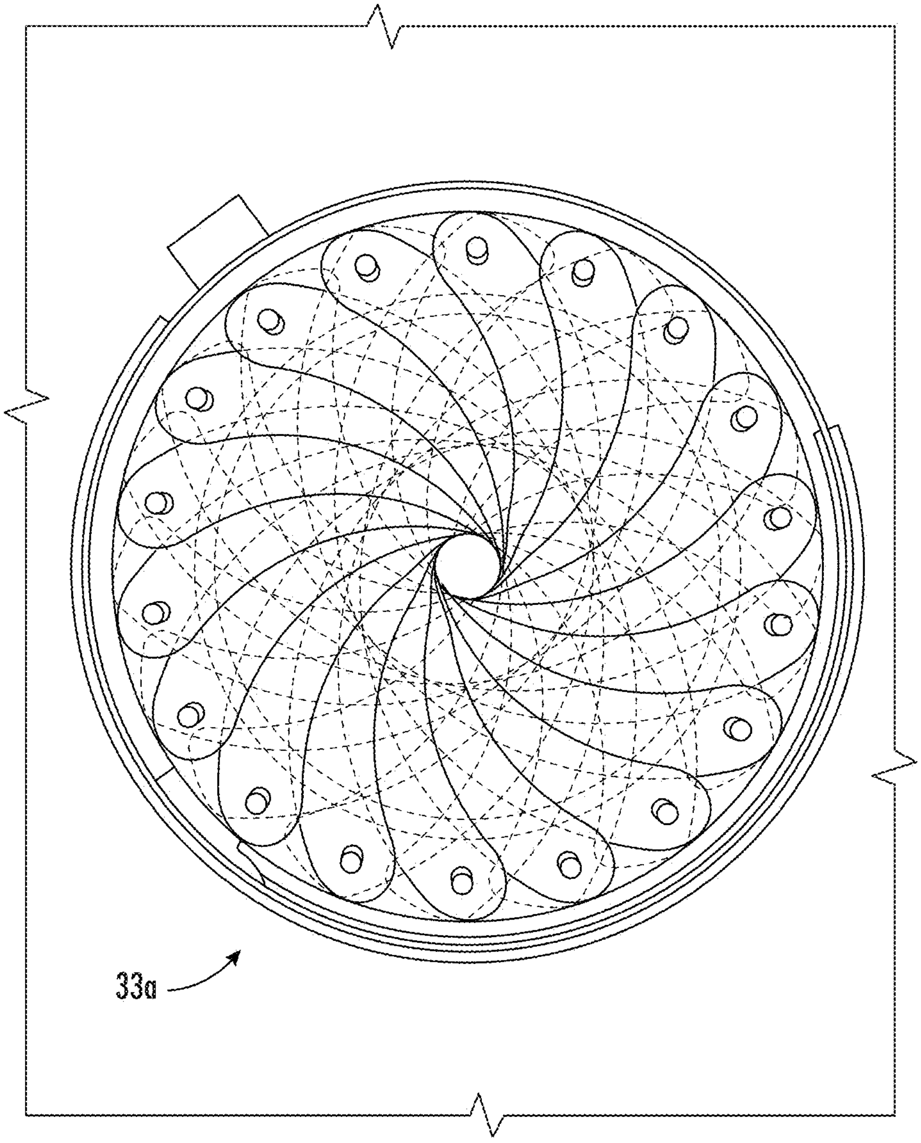

The simple sliding door of the preferred embodiment, can be driven by a mechanism such as a timing belt or screw drive. The door can take many forms, such as a mechanical Iris 33A of FIGS. 33A and 33B.

Cartridge

Figure 35:
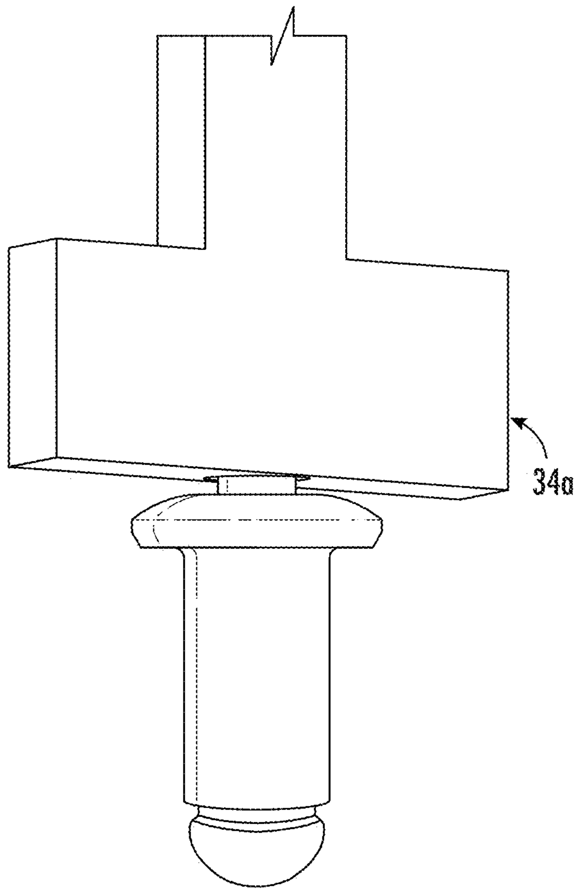
FIG. 35 is a view of the flanged base of the slide of the glove donning apparatus shown in FIG. 1.
Figure 36:
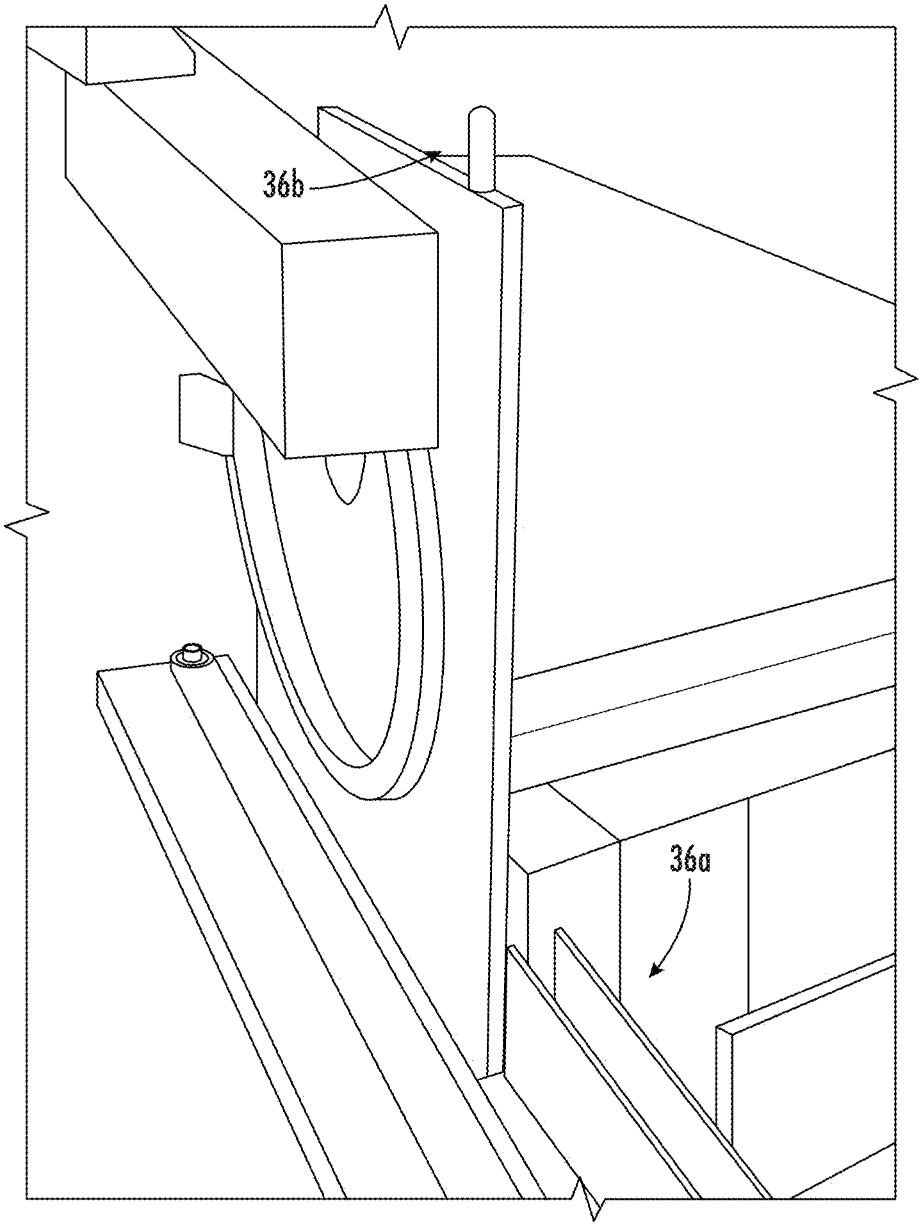
FIG. 36 is a view of the pins and tracks of the slide guiding system of the glove donning apparatus shown in FIG. 1.

In the preferred embodiment, clips 36*a* are riveted to the belt and used to retain a slide having a flanged base shown in FIG. 35. After a glove is loaded into a slide, the slide is slid into the clip 36*a* from the side, and the belt is advanced, ready to load another slide. Each clip 36*a* is loaded with a slide until the cartridge capacity is reached. The slides are prevented from sliding out of the clips 36*a* by the outer walls of the cartridge. Each cartridge is basically a box, containing the clips 36*a*, timing belt, belt pulleys, and slides (when loaded).

Figure 34:
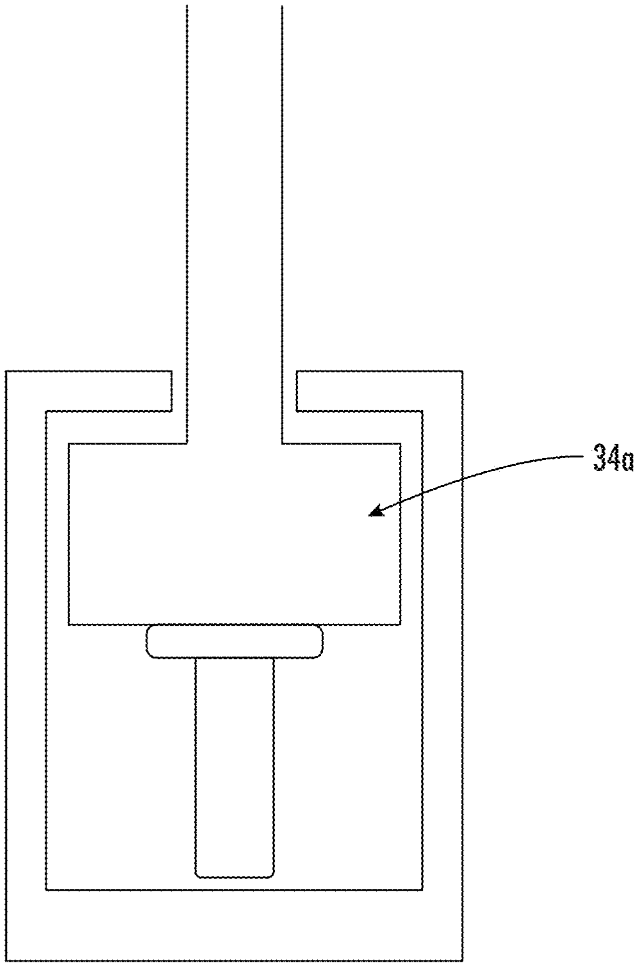
FIG. 34 is a profile view of a clip with a slide inside, of the glove donning apparatus shown in FIG. 1.

FIG. 34 models a profile view of a clip 36*a* with a slide inside. The flanged base of the slide 34*a* serves to retain the slide in the clip 36*a*, while allowing it to be slid into and out of the side of the clip 36*a*.

Figure 37:
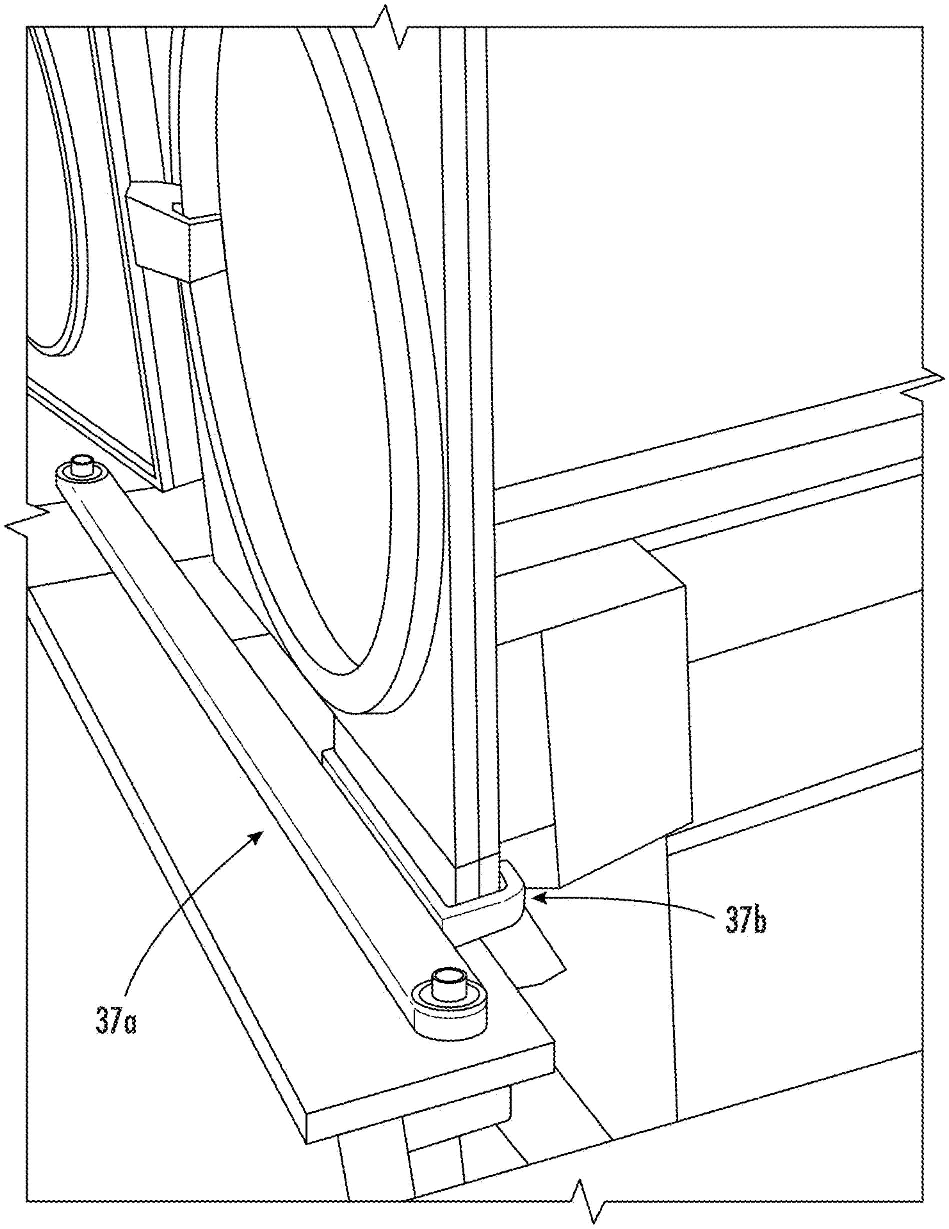
FIG. 37 is a view of the slide driving system of the glove donning apparatus shown in FIG. 1.

The cartridge is snapped into a large slot on the Glove Box base cabinet, which causes the upper-most slide position of the cartridge to be aligned with the slide track grooves 29A in FIG. 29, which lead the slides into place for glove donning. The tracks guide the 4 slide pins that are attached to the top and bottom of the slide. The slide is pushed out of its clip 36*a* and into the tracks by another timing belt—the slide driver belt 37*a* in FIG. 37, which extends into the cartridge, as the cartridge is being installed.

The slide driver belt 37*a* has an attached protrusion (37*b*), which engages the back of the slide, near its base, and pushes the slide along the clip 36*a*, which acts as a bottom guide track, until the slide meets the slide track grooves 29A in the "front porch". The slide track grooves 29A are flared at the point where the slides enter to help ensure that the slide pins smoothly enter the tracks. After the slide is completely onto the front porch, and out of the cartridge, the clip 36*a* that it was in, is now empty, and therefore free to pass underneath the slide driver system, as the cartridge timing belt advances to the next slide.

When a user dons gloves, initiating another cycle, the stepper motor advances the timing belt in the cartridge to move the next slide into the uppermost position, ready to be pushed into place for the next cycle.

Figure 39:
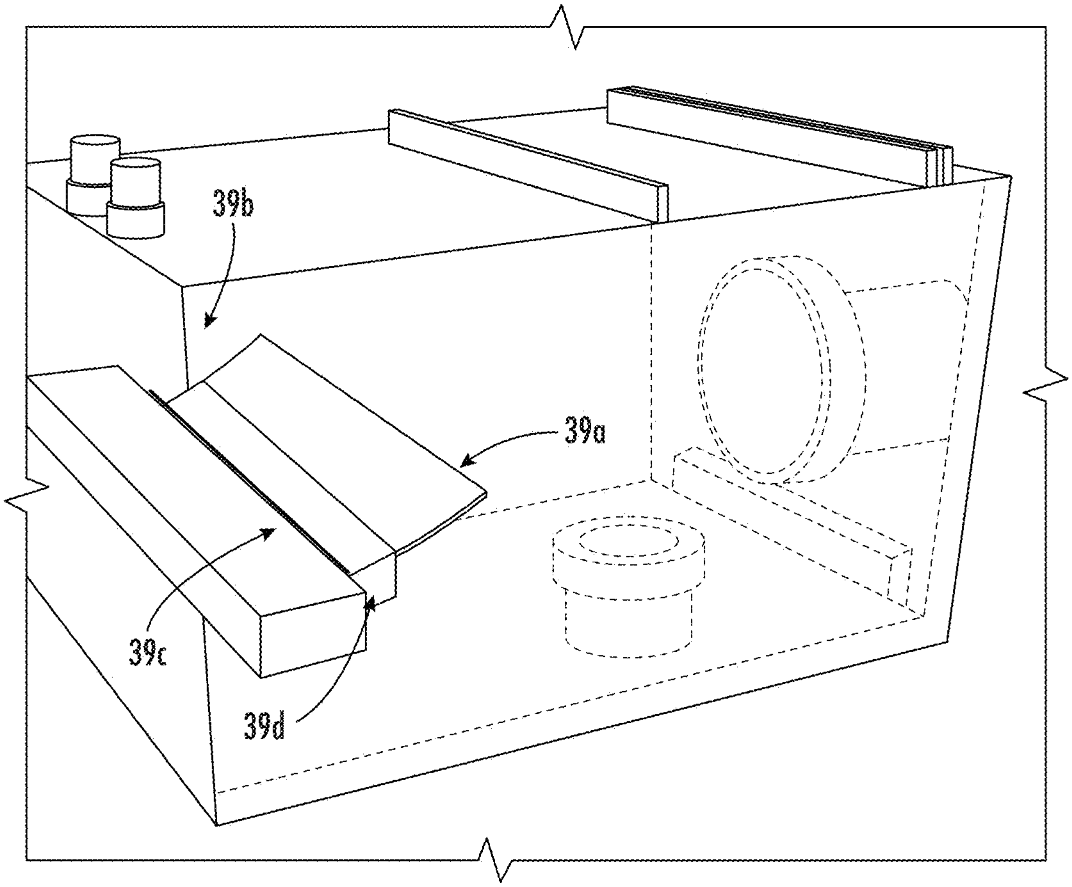
FIG. 39 is a view of the on-deck slide upper track engagement system of the glove donning apparatus shown in FIG. 1.

The top pins of the uppermost slide, shown as 17D and 36*b*, are slid into the upper front porch tracks, via a hinged flap 39*a* of FIG. 39. When the top slide is advanced, the pins wedge the flap up until they pass the break in the flap 39*d*, allowing the flap to drop, trapping the slide's upper pins in the flap's channel 39*d*, formed by the flap 39*a* and the backstop 39*c*, which are positioned to guide the top pins into the upper porch channel position 39*b*.

Wedged Ridges on Slides

In one embodiment, two slide tracks are required along the bottom, and 2 along the top, in order to guide the slide's 4 pins such that the slide does not scrape against the gasket while sliding into place. This can be seen in FIG. 25 as the bottom front track 25*a*, and the bottom back track 25*b*. To minimize scraping the slide on the gasket, the shape of the tracks prevents the slide from touching the gasket until its final moment of travel.

Figure 40:
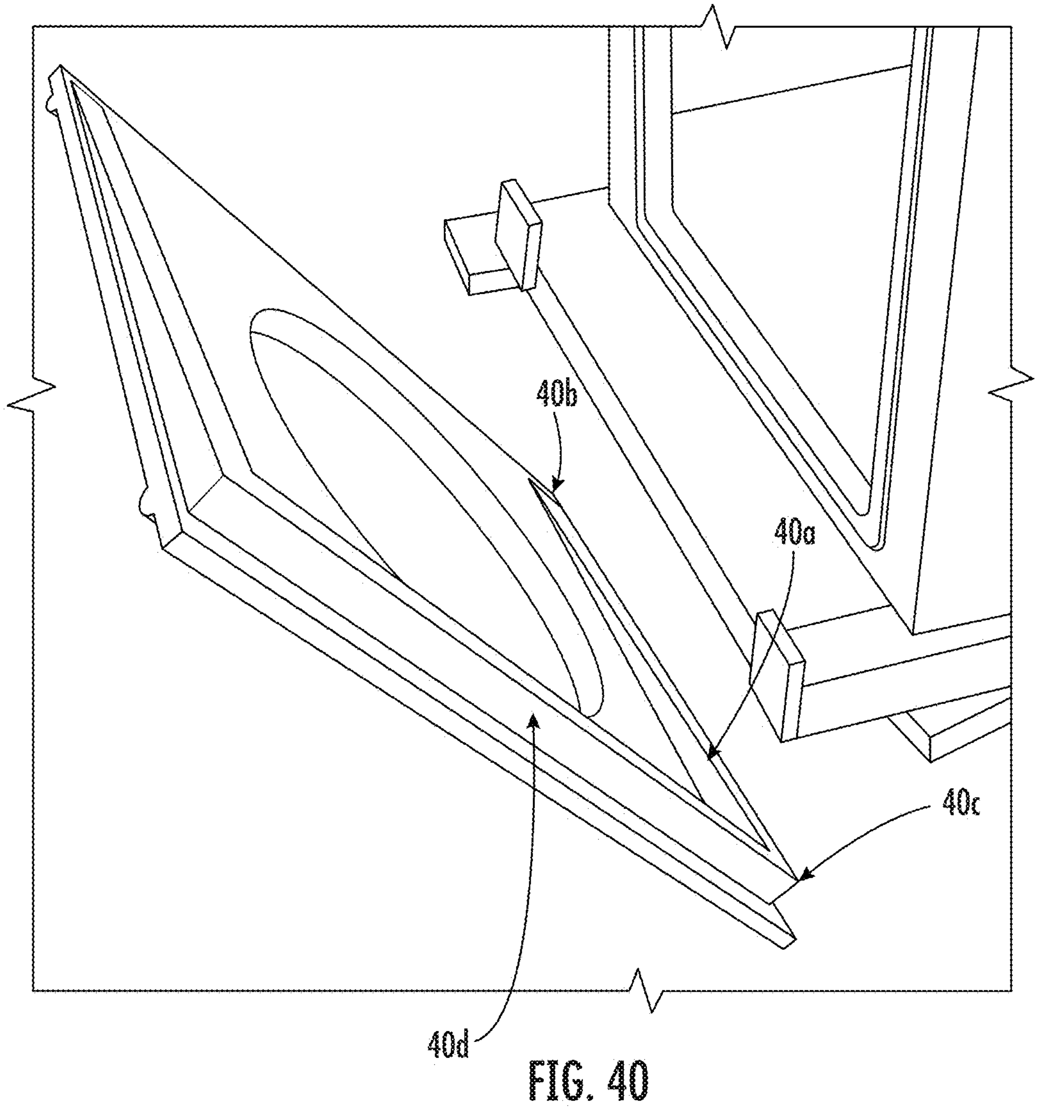
FIG. 40 is a view of a slide with wedged ridges for gasket sealing in another embodiment.
Figure 41:
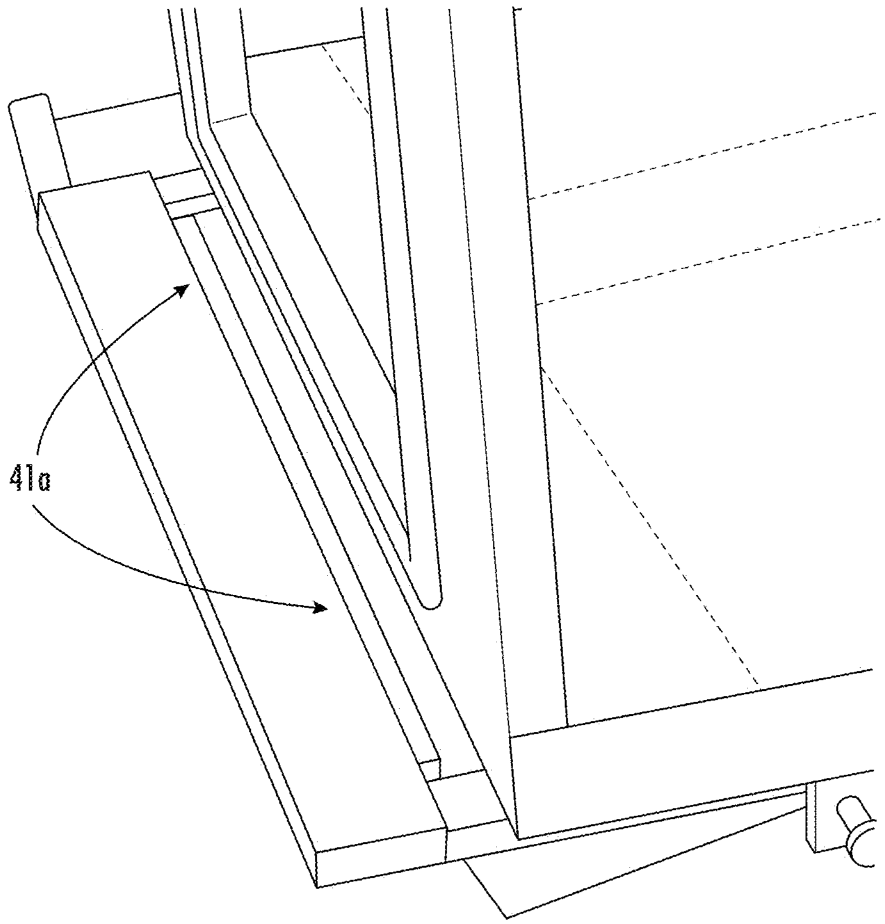
FIG. 41 is a view of a single track designed to work with the wedged ridges of FIG. 40 in another embodiment.

In another embodiment, the slides have wedges to meet the gasket, allowing both front and back slide pins to use the same track. The bottom single track is labeled 41*a* in FIG. 41. FIG. 40 shows the slide with wedged ridges. There is a top wedged ridge along the top of the slide and also the bottom wedged ridge 40*a*, which tapers up from zero at point 40*b* to about ¼" at point 40*c*. Another ridge 40*d* (not wedged) connects the top wedged ridge to the bottom wedged ridge. This slide design, in combination with the single track coming in at a slight angle, allows the wedges to meet the gasket only upon reaching the slide's final position.

Figure 42:
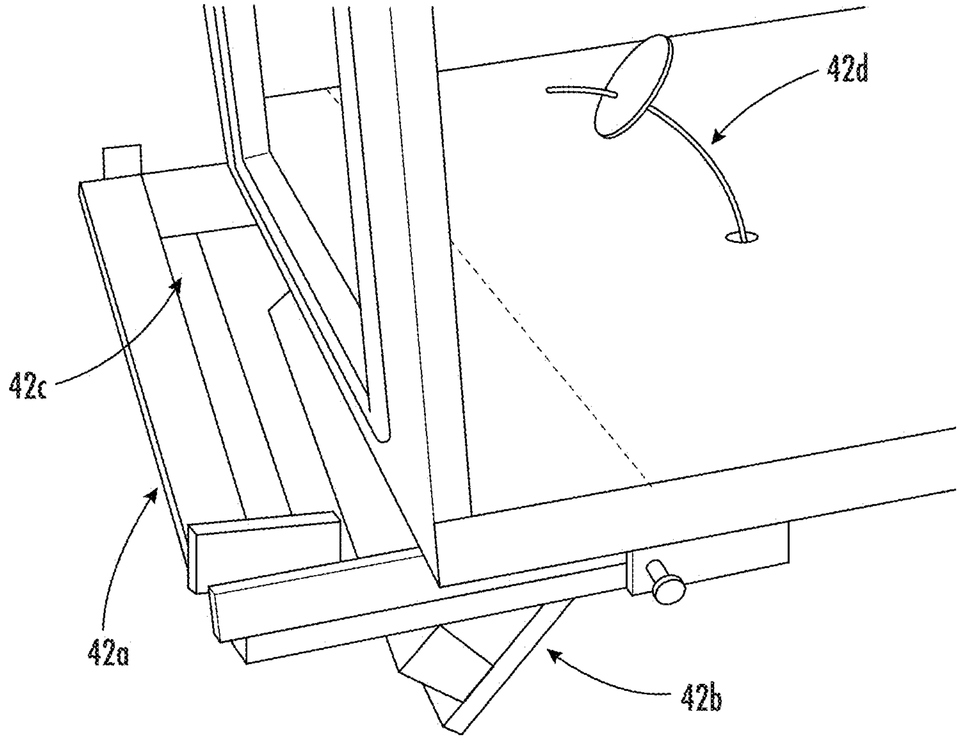
FIG. 42 is a view of a trap door designed to work with the single track of FIG. 41 in another embodiment.
Figure 43:
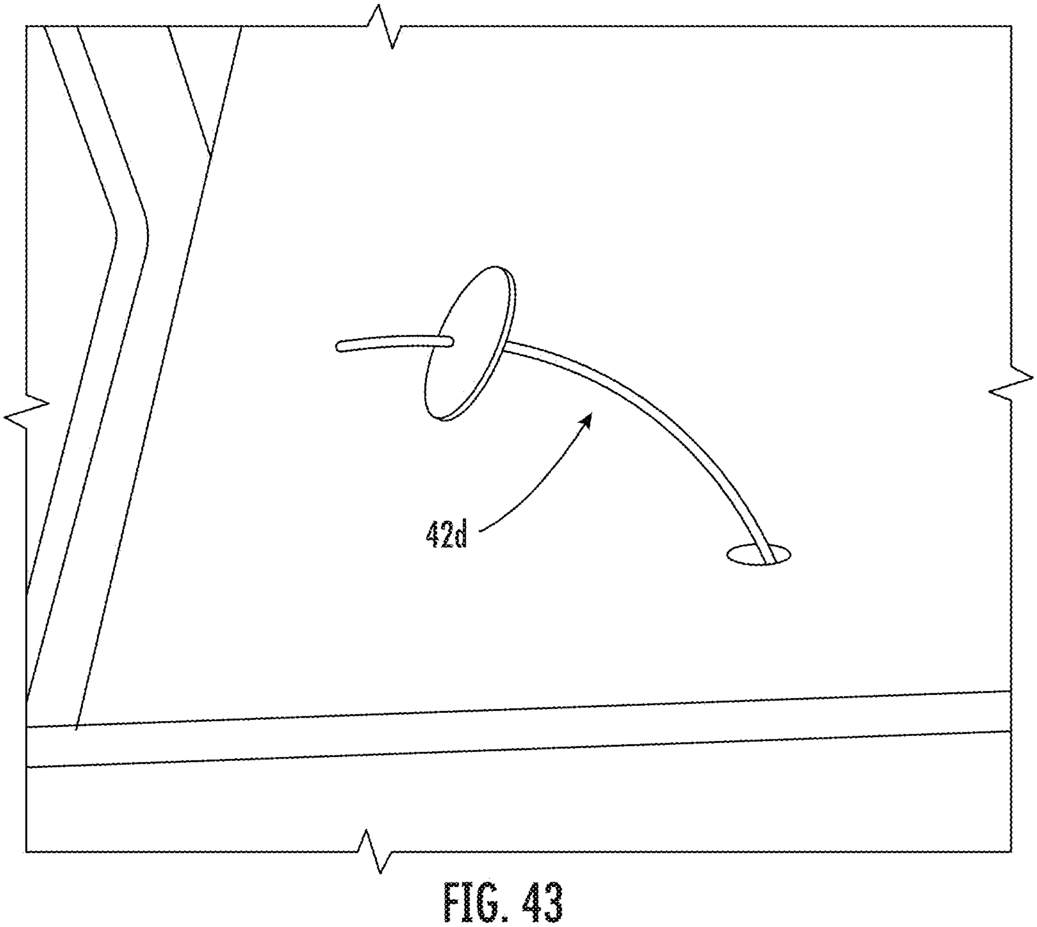
FIG. 43 is a view of a slide flap closing mechanism connected to the door shown in FIG. 42 in another embodiment.
Figure 44:
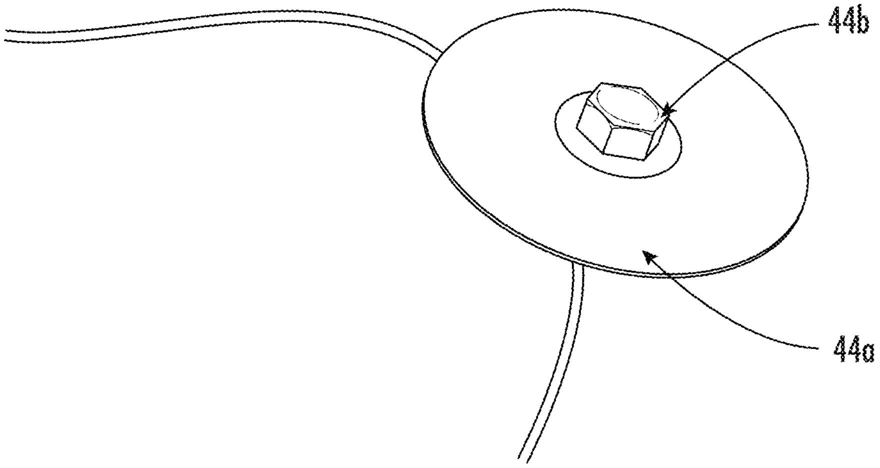
FIG. 44 is a view of a hook head and gasket designed to work with the slide flap closing mechanism of FIG. 43 in another embodiment.

FIG. 42 shows the trap door of one embodiment. The door is made in 2 parts, front half-door 42*a* and back half-door 42*b*, which meet at the track itself, so that the pins do not get pinched or caught when the door opens. A notch (42*c*) allows the doors to hinge away from each other without bumping into each other due to their thicknesses. A stiff hook 42*d* extends from the back half-door into the vacuum chamber through a hole in the floor. When the door drops, the hook is automatically pushed up into the chamber, which pushes the slide flap closed, so that it will fall unimpeded down through the trap door. FIG. 44 shows a design of a gasket, modeled by the disk 44*a* that keeps the hook hole sealed when there is a vacuum in the chamber. The rim of the gasket 44*a* is glued to the floor of the chamber, while the center of the gasket flexes easily, such that the chamber vacuum pulls the gasket up to meet the rubber seal attached to the underside of the hook's head 44*b*, thereby sealing the hole. The hook's head 44*b* is rounded, to better meet and push the slide flap up.

What is claimed is:

1. A glove donning apparatus, comprising:

a vacuum chamber;

a slide configured to receive a glove, the slide moveable relative to the vacuum chamber and configured to be positioned at an opening of the vacuum chamber; and bellows in communication with the vacuum chamber, the bellows moveable between a contracted position and an expanded position;

at least one weight coupled to the bellows and moveable between a top position and a bottom position;

wherein release of the at least one weight from the top position causes the at least one weight to be drawn downward by force of gravity toward the bottom position and results in movement of the bellows toward the expanded position such that air is drawn out of the vacuum chamber, thereby creating a vacuum condition within the vacuum chamber and causing the glove to inflate.

2. The glove donning apparatus of claim 1, the at least one weight further comprising removable weights positioned on a base of the bellows.

3. The glove donning apparatus of claim 1 further comprising an elevator configured to lift the bellows and the at least one weight from the bottom position to the top position.

4. The glove donning apparatus of claim 1 further comprising at least one latch configured to retain the bellows and the at least one weight in the top position, wherein release of the latch releases the at least one weight from the top position.

5. The glove donning apparatus of claim 4 further comprising a controller configured to send a signal to an actuator to release the latch, wherein release of the latch causes the at least one weight to be forced downward under the force of gravity from the top position toward the bottom position.

6. The glove donning apparatus of claim 1 further comprising a button positioned in the vacuum chamber opposite the opening, wherein the button is configured for depression by a hand of a user positioned within the inflated glove.

7. The glove donning apparatus of claim 6 further comprising a cuff release mechanism wherein depression of the button causes the cuff release mechanism to release the glove from the slide such that the vacuum condition in the vacuum chamber is released, thereby deflating the glove and positioning the glove on the hand of the user within the vacuum chamber.

8. The glove donning apparatus of claim 6 wherein the opening in the vacuum chamber is a front opening.

9. The glove donning apparatus of claim 8 wherein the front opening is a first front opening of the vacuum chamber, the slide is a first slide, and the glove is a first glove, the glove donning apparatus further comprising a second front opening to the vacuum chamber and a second slide configured to receive a second glove, the second slide moveable relative to the vacuum chamber and configured to be positioned at the second front opening of the vacuum chamber.

10. A glove donning apparatus, comprising:

a vacuum chamber including an opening; and a slide including a cuff ring configured to receive a glove, the slide moveable relative to the vacuum chamber and configured to be positioned at the opening of the vacuum chamber to cover the opening of the vacuum chamber, the slide further including a hinged flap configured to hold the glove in place, the hinged flap held shut magnetically;

wherein, when the slide is positioned at the opening of the vacuum chamber with the glove positioned on the cuff ring, a vacuum condition existing within the vacuum chamber draws the slide inward against the vacuum chamber such that the slide covers the opening of the vacuum chamber and the vacuum condition causes the glove to inflate within the vacuum chamber.

11. The glove donning apparatus of claim 10 further comprising a vacuum seal gasket surrounding the opening and positioned between the slide and the vacuum chamber when the vacuum chamber draws the slide inward against the vacuum chamber.

12. The glove donning apparatus of claim 10 further comprising a cuff release mechanism positioned on the slide.

13. The glove donning apparatus of claim 12 wherein the cuff release mechanism is a cuff release tab or a releasing ring, the cuff release tab configured to lever a cuff of the glove away from the cuff ring, and the releasing ring configured to encircle the cuff ring and release the glove from the cuff ring when in a release position.

14. The glove donning apparatus of claim 10 wherein the slide is one of a plurality of slides in a cartridge of slides, each of the plurality of slides configured to be sequentially moved from the cartridge to the opening of the vacuum chamber.

15. The glove donning apparatus of claim 14 each of the plurality of slides further including a guide shaft configured to slide along a groove when the slide is moved from the cartridge to the opening of the vacuum chamber.

16. The glove donning apparatus of claim 10 wherein the slide is defined by a rigidity that is sufficient to prevent the slide from bending and being drawn into the vacuum chamber when the vacuum condition exists within the vacuum chamber.

* * * * *